(12) United States Patent
Angel et al.

(10) Patent No.: US 8,393,328 B2
(45) Date of Patent: Mar. 12, 2013

(54) AIRWAY ASSEMBLY AND METHODS OF USING AN AIRWAY ASSEMBLY

(75) Inventors: Luis F. Angel, San Antonio, TX (US); Jeffrey N. Steinmetz, Hillsboro, OR (US)

(73) Assignee: BiO2 Medical, Inc., San Antonio, TX (US)

( * ) Notice: Subject to any disclaimer, the term of this patent is extended or adjusted under 35 U.S.C. 154(b) by 1239 days.

(21) Appl. No.: 11/966,767

(22) Filed: Dec. 28, 2007

(65) Prior Publication Data

US 2008/0156323 A1 Jul. 3, 2008

Related U.S. Application Data

(63) Continuation-in-part of application No. 10/569,397.

(60) Provisional application No. 60/497,140, filed on Aug. 22, 2003.

(51) Int. Cl.
*A61M 16/00* (2006.01)
*A61M 16/04* (2006.01)

(52) U.S. Cl. ......... 128/207.14; 128/200.26; 128/202.27; 128/204.18; 128/207.15; 128/912; 600/108; 600/120; 600/121

(58) Field of Classification Search ............. 128/207.14, 128/200.26, 202.27, 204.18, 207.18, 912; 600/120, 121; 606/108
See application file for complete search history.

(56) References Cited

U.S. PATENT DOCUMENTS

| 3,490,457 | A | * | 1/1970 | Petersen | 604/105 |
|---|---|---|---|---|---|
| 3,616,799 | A | * | 11/1971 | Sparks | 128/207.15 |
| 3,671,979 | A | | 6/1972 | Moulopoulos | 3/1 |
| 3,880,168 | A | | 4/1975 | Berman | 128/351 |
| 4,231,365 | A | * | 11/1980 | Scarberry | 128/207.15 |
| 4,334,534 | A | * | 6/1982 | Ozaki | 128/207.15 |
| 4,738,666 | A | * | 4/1988 | Fuqua | 604/514 |
| 4,901,731 | A | | 2/1990 | Millar | 128/675 |
| 4,969,891 | A | | 11/1990 | Gewertz | 606/200 |
| 4,976,261 | A | * | 12/1990 | Gluck et al. | 128/207.15 |
| 5,020,534 | A | * | 6/1991 | Pell et al. | 128/207.15 |
| 5,033,466 | A | | 7/1991 | Weymuller, Jr. | 128/207.15 |
| 5,053,008 | A | | 10/1991 | Bajaj | 604/104 |
| 5,112,347 | A | | 5/1992 | Taheri | 606/200 |

(Continued)

FOREIGN PATENT DOCUMENTS

WO 97/17100 5/1997
WO 97/42879 11/1997

(Continued)

OTHER PUBLICATIONS

International Search Report, pp. 1-4 (Mar. 30, 2009).

(Continued)

*Primary Examiner* — Clinton T Ostrup
(74) *Attorney, Agent, or Firm* — J. Peter Paredes; Rosenbaum IP

(57) ABSTRACT

Many embodiments of an airway assembly and methods of using an airway assembly are disclosed. In one embodiment, an airway assembly includes an outer tube, an inner tube disposed coaxially with the outer tube, and a seal disposed on the inner tube. The seal is movable between a collapsed position and an expanded position where the seal engages an airway. Another embodiment is an airway assembly that includes an outer tube having a proximal portion and a distal portion, and an inner tube disposed coaxially with the outer tube. The inner tube has a proximal portion and a distal portion. The proximal portion of the outer tube has an outer diameter that is larger than an outer diameter of the distal portion of the outer tube.

30 Claims, 25 Drawing Sheets

U.S. PATENT DOCUMENTS

| | | | |
|---|---|---|---|
| 5,163,941 A | 11/1992 | Garth et al. | 606/108 |
| 5,190,561 A * | 3/1993 | Graber | 606/127 |
| 5,201,757 A | 4/1993 | Heyn et al. | 606/200 |
| 5,259,371 A * | 11/1993 | Tonrey | 128/200.26 |
| 5,423,830 A * | 6/1995 | Schneebaum et al. | 606/115 |
| 5,429,127 A | 7/1995 | Kolobow | 128/207.14 |
| 5,540,224 A | 7/1996 | Buret et al. | 128/207.14 |
| 5,545,214 A * | 8/1996 | Stevens | 606/191 |
| 5,549,626 A | 8/1996 | Miller et al. | 606/200 |
| 5,556,376 A * | 9/1996 | Yoon | 604/15 |
| 5,624,396 A | 4/1997 | McNamara et al. | 604/93 |
| 5,643,282 A * | 7/1997 | Kieturakis | 606/114 |
| 5,645,083 A * | 7/1997 | Essig et al. | 128/898 |
| 5,707,389 A | 1/1998 | Louw et al. | 606/200 |
| 5,715,829 A | 2/1998 | Arand et al. | 128/673 |
| 5,766,151 A | 6/1998 | Valley et al. | 604/96 |
| 5,769,816 A | 6/1998 | Barbut et al. | 604/96 |
| 5,791,341 A | 8/1998 | Bullard | 128/207.15 |
| 5,795,322 A | 8/1998 | Boudewijn | 604/22 |
| 5,795,325 A | 8/1998 | Valley et al. | 604/53 |
| 5,797,920 A | 8/1998 | Kim | 606/108 |
| 5,814,064 A | 9/1998 | Daniel et al. | 606/200 |
| 5,833,650 A | 11/1998 | Imran | 604/53 |
| 5,848,964 A | 12/1998 | Samuels | 600/200 |
| 5,879,499 A | 3/1999 | Corvi | 156/175 |
| 5,893,868 A | 4/1999 | Hanson et al. | 606/198 |
| 5,925,016 A | 7/1999 | Chornenky et al. | 604/96 |
| 5,947,994 A | 9/1999 | Louw et al. | 606/200 |
| 5,947,995 A | 9/1999 | Samuels | 606/200 |
| 5,954,636 A | 9/1999 | Schwartz et al. | 600/120 |
| 5,954,742 A | 9/1999 | Osypka | 606/198 |
| 5,976,172 A | 11/1999 | Homsma et al. | 606/200 |
| 5,980,478 A | 11/1999 | Gorsuch et al. | 604/4 |
| 5,980,555 A | 11/1999 | Barbut et al. | 600/200 |
| 5,989,281 A | 11/1999 | Barbut et al. | 606/200 |
| 6,007,544 A | 12/1999 | Kim | 606/108 |
| 6,051,014 A | 4/2000 | Jang | 606/200 |
| 6,086,605 A | 7/2000 | Barbut et al. | 606/200 |
| 6,090,097 A | 7/2000 | Barbut et al. | 604/511 |
| 6,117,154 A | 9/2000 | Barbut et al. | 606/181 |
| 6,135,991 A | 10/2000 | Muni et al. | 604/509 |
| 6,136,016 A | 10/2000 | Barbut et al. | 606/200 |
| 6,152,909 A | 11/2000 | Bagaoisan et al. | 604/523 |
| 6,165,179 A | 12/2000 | Cathcart et al. | 606/108 |
| 6,178,968 B1 | 1/2001 | Louw et al. | 128/898 |
| 6,224,627 B1 | 5/2001 | Armstrong et al. | 623/1.23 |
| 6,231,544 B1 | 5/2001 | Tsugita et al. | 604/104 |
| 6,235,045 B1 | 5/2001 | Barbut et al. | 606/200 |
| 6,251,093 B1 | 6/2001 | Valley et al. | 604/96 |
| 6,270,477 B1 | 8/2001 | Bagaoisan et al. | 604/96.01 |
| 6,277,138 B1 | 8/2001 | Levinson et al. | 606/200 |
| 6,287,321 B1 | 9/2001 | Jang | 606/200 |
| 6,315,792 B1 | 11/2001 | Armstrong et al. | 623/1.13 |
| 6,336,934 B1 | 1/2002 | Gilson et al. | 606/200 |
| 6,344,049 B1 | 2/2002 | Levinson et al. | 606/200 |
| 6,344,053 B1 | 2/2002 | Boneau | 623/1.11 |
| 6,379,373 B1 | 4/2002 | Sawhney et al. | 606/193 |
| 6,383,196 B1 | 5/2002 | Leslie et al. | 606/114 |
| 6,423,086 B1 | 7/2002 | Barbut et al. | 606/200 |
| 6,432,122 B1 | 8/2002 | Gilson et al. | 606/200 |
| 6,443,971 B1 | 9/2002 | Boylan et al. | 606/200 |
| 6,454,741 B1 | 9/2002 | Muni et al. | 604/96.01 |
| 6,511,503 B1 | 1/2003 | Burkett et al. | 623/1.11 |
| 6,537,294 B1 | 3/2003 | Boyle et al. | 606/200 |
| 6,537,296 B2 | 3/2003 | Levinson et al. | 606/200 |
| 6,544,279 B1 | 4/2003 | Hopkins et al. | 606/200 |
| 6,547,788 B1 | 4/2003 | Maguire et al. | 604/41 |
| 6,561,996 B1 | 5/2003 | Gorsuch | 604/6.09 |
| 6,569,148 B2 | 5/2003 | Bagaoisan et al. | 604/509 |
| 6,585,639 B1 | 7/2003 | Kotmel et al. | 600/116 |
| 6,589,264 B1 | 7/2003 | Barbut et al. | 606/200 |
| 6,592,546 B1 | 7/2003 | Barbut et al. | 604/96.01 |
| 6,596,011 B2 | 7/2003 | Johnson et al. | 606/200 |
| 6,616,680 B1 | 9/2003 | Theilen | 606/200 |
| 6,623,507 B2 | 9/2003 | Saleh | 606/200 |
| 6,635,070 B2 | 10/2003 | Leeflang et al. | 606/200 |
| 6,669,708 B1 | 12/2003 | Nissenbaum et al. | 606/153 |
| 6,685,722 B1 | 2/2004 | Rosenbluth et al. | 606/200 |
| 6,689,148 B2 | 2/2004 | Sawhney et al. | 606/193 |
| 6,692,512 B2 | 2/2004 | Jang | 606/200 |
| 6,726,651 B1 | 4/2004 | Robinson et al. | 604/101.01 |
| 6,726,702 B2 | 4/2004 | Khosravi | 606/200 |
| 6,749,619 B2 | 6/2004 | Ouriel et al. | 606/200 |
| 6,755,813 B2 | 6/2004 | Ouriel et al. | 604/537 |
| 6,780,193 B2 | 8/2004 | Leslie et al. | 606/114 |
| 6,805,692 B2 | 10/2004 | Muni et al. | 604/509 |
| 6,869,431 B2 | 3/2005 | Maguire et al. | 604/41 |
| 6,885,115 B2 | 4/2005 | Hatori et al. | 307/80 |
| 6,887,257 B2 | 5/2005 | Salahieh et al. | 606/200 |
| 6,913,600 B2 | 7/2005 | Valley et al. | 604/509 |
| 6,978,784 B2 | 12/2005 | Pekar | 128/207.14 |
| 6,986,778 B2 | 1/2006 | Zadno-Azizi | 606/200 |
| 7,011,672 B2 | 3/2006 | Barbut et al. | 606/200 |
| 7,060,082 B2 | 6/2006 | Goll et al. | 606/200 |
| 7,108,708 B2 | 9/2006 | Cheng et al. | 606/200 |
| 7,125,414 B2 | 10/2006 | Blackledge et al. | 606/200 |
| 7,144,408 B2 | 12/2006 | Keegan et al. | 606/200 |
| 7,150,737 B2 | 12/2006 | Purdy et al. | 604/506 |
| 7,153,320 B2 | 12/2006 | Euteneuer et al. | 606/200 |
| 7,163,520 B2 | 1/2007 | Bernard et al. | 604/6.9 |
| 7,166,570 B2 | 1/2007 | Hunter et al. | 514/2 |
| 7,220,270 B2 | 5/2007 | Sawhney et al. | 606/193 |
| 7,261,727 B2 | 8/2007 | Thielen | 606/200 |
| 2001/0001812 A1 | 5/2001 | Valley et al. | 604/96.01 |
| 2001/0031981 A1 | 10/2001 | Evans et al. | 606/200 |
| 2002/0062134 A1 | 5/2002 | Barbut et al. | 606/200 |
| 2002/0072730 A1 | 6/2002 | McGill et al. | 604/525 |
| 2002/0082525 A1 | 6/2002 | Oslund et al. | 600/585 |
| 2002/0082636 A1 | 6/2002 | Sawhney et al. | 606/193 |
| 2002/0091407 A1 | 7/2002 | Zadno-Azizi et al. | 606/200 |
| 2002/0107479 A1 | 8/2002 | Bates et al. | 604/96.01 |
| 2002/0188313 A1 | 12/2002 | Johnson et al. | 606/200 |
| 2003/0009146 A1 | 1/2003 | Muni et al. | 604/500 |
| 2003/0032941 A1 | 2/2003 | Boyle et al. | 604/533 |
| 2003/0050600 A1 | 3/2003 | Reesemann et al. | 604/101.01 |
| 2003/0093110 A1 | 5/2003 | Vale | 606/200 |
| 2003/0097082 A1 | 5/2003 | Purdy et al. | 606/594 |
| 2003/0097094 A1 | 5/2003 | Ouriel et al. | 604/93.01 |
| 2003/0125764 A1 | 7/2003 | Brady et al. | 606/200 |
| 2003/0135198 A1 * | 7/2003 | Berhow et al. | 604/524 |
| 2003/0176889 A1 | 9/2003 | Boyle et al. | 606/200 |
| 2003/0187495 A1 | 10/2003 | Cully et al. | 623/1.15 |
| 2003/0203031 A1 | 10/2003 | Shah | 424/485 |
| 2003/0208222 A1 | 11/2003 | Zadno-Azizi | 606/194 |
| 2003/0212434 A1 | 11/2003 | Thielen | 606/200 |
| 2003/0233117 A1 | 12/2003 | Adams et al. | 606/200 |
| 2004/0006367 A1 | 1/2004 | Johnson et al. | 606/200 |
| 2004/0011740 A1 | 1/2004 | Bernard et al. | 210/646 |
| 2004/0044302 A1 | 3/2004 | Bernard et al. | 604/6.09 |
| 2004/0102806 A1 | 5/2004 | Broome et al. | 606/200 |
| 2004/0153112 A1 | 8/2004 | Nissenbaum et al. | 606/185 |
| 2004/0158276 A1 | 8/2004 | Barbut et al. | 606/200 |
| 2004/0162576 A1 | 8/2004 | Barbut et al. | 606/200 |
| 2004/0199177 A1 | 10/2004 | Kim | 606/108 |
| 2004/0220612 A1 | 11/2004 | Swainston et al. | 606/200 |
| 2004/0236170 A1 | 11/2004 | Kim | 600/16 |
| 2004/0254528 A1 | 12/2004 | Adams et al. | 604/96.01 |
| 2005/0027236 A1 | 2/2005 | Douk et al. | 604/40 |
| 2005/0038503 A1 | 2/2005 | Greenhalgh et al. | 623/1.42 |
| 2005/0080445 A1 | 4/2005 | Sawhney et al. | 606/193 |
| 2005/0085769 A1 | 4/2005 | MacMahon et al. | 604/96.01 |
| 2005/0085841 A1 | 4/2005 | Eversull et al. | 606/190 |
| 2005/0107817 A1 | 5/2005 | White et al. | 606/191 |
| 2005/0133046 A1 | 6/2005 | Becker et al. | 128/898 |
| 2005/0142163 A1 | 6/2005 | Hunter et al. | 424/423 |
| 2005/0145258 A1 | 7/2005 | Dong | 128/898 |
| 2005/0147562 A1 | 7/2005 | Hunter et al. | 424/9.5 |
| 2005/0147599 A1 | 7/2005 | Hunter et al. | 424/94.63 |
| 2005/0147643 A1 | 7/2005 | Hunter et al. | 424/423 |
| 2005/0148512 A1 | 7/2005 | Hunter et al. | 514/12 |
| 2005/0148997 A1 | 7/2005 | Valley et al. | 604/509 |
| 2005/0158274 A1 | 7/2005 | Hunter et al. | 424/78.38 |
| 2005/0169958 A1 | 8/2005 | Hunter et al. | 424/423 |
| 2005/0169959 A1 | 8/2005 | Hunter et al. | 424/423 |
| 2005/0175657 A1 | 8/2005 | Hunter et al. | 424/422 |
| 2005/0177186 A1 | 8/2005 | Cully et al. | 606/200 |
| 2005/0186247 A1 | 8/2005 | Hunter et al. | 424/423 |

| | | | | | |
|---|---|---|---|---|---|
| 2005/0191248 A1 | 9/2005 | Hunter et al. ................ 424/50 | WO | 00/09190 | 2/2000 |
| 2005/0192620 A1 | 9/2005 | Cully et al. ................ 606/200 | WO | 01/13983 | 3/2001 |
| 2005/0197624 A1 | 9/2005 | Goodson, IV et al. ..... 604/96.01 | WO | 01/65936 | 9/2001 |
| 2005/0205097 A1 | 9/2005 | Kyle, Jr. ................ 128/207.14 | WO | 02/30271 | 4/2002 |
| 2005/0245962 A1 | 11/2005 | Adams et al. ................ 606/194 | WO | 02/39878 | 5/2002 |
| 2005/0261733 A1 | 11/2005 | Cheng et al. ................ 606/200 | WO | 02/40090 | 5/2002 |
| 2005/0267408 A1 | 12/2005 | Grandt et al. ........... 604/103.04 | WO | 03/015859 | 2/2003 |
| 2005/0267442 A1 | 12/2005 | Von Oepen ................ 604/509 | WO | 03/084437 | 10/2003 |
| 2005/0277976 A1 | 12/2005 | Galdonik et al. ............ 606/200 | WO | 2004/014240 | 2/2004 |
| 2005/0283182 A1 | 12/2005 | Pierce et al. ................ 606/200 | WO | 2004/054650 | 7/2004 |
| 2006/0095002 A1 | 5/2006 | Soltesz et al. ................ 604/39 | WO | 2004/060465 | 7/2004 |
| 2006/0135961 A1 | 6/2006 | Rosenman et al. .......... 606/108 | WO | 2004/098674 | 11/2004 |
| 2006/0189921 A1 | 8/2006 | Galdonik et al. ............ 604/27 | WO | 2005/011786 | 2/2005 |
| 2006/0190025 A1 | 8/2006 | Lehe et al. ................ 606/200 | WO | 2005/023358 | 3/2005 |
| 2006/0200191 A1 | 9/2006 | Zadno-Azizi ................ 606/200 | WO | 2005/046746 | 5/2005 |
| 2006/0229657 A1 | 10/2006 | Wasicek et al. ............. 606/200 | WO | 2005/058384 | 6/2005 |
| 2006/0240063 A9 | 10/2006 | Hunter et al. ................ 424/423 | WO | 2005/065079 | 7/2005 |
| 2006/0240064 A9 | 10/2006 | Hunter et al. ................ 424/423 | WO | 2005/074520 | 8/2005 |
| 2006/0241675 A1 | 10/2006 | Johnson et al. ............ 606/200 | WO | 2005/091910 | 10/2005 |
| 2006/0241676 A1 | 10/2006 | Johnson et al. ............ 606/200 | WO | 2005/118044 | 12/2005 |
| 2006/0241677 A1 | 10/2006 | Johnson et al. ............ 606/200 | WO | 2005/118045 | 12/2005 |
| 2006/0241678 A1 | 10/2006 | Johnson et al. ............ 606/200 | WO | 2005/118050 | 12/2005 |
| 2006/0241679 A1 | 10/2006 | Johnson et al. ............ 606/200 | WO | 2006/065949 | 6/2006 |
| 2006/0241680 A1 | 10/2006 | Johnson et al. ............ 606/200 | WO | 2006/074163 | 7/2006 |
| 2006/0248871 A1 | 11/2006 | Johnson et al. ............ 57/58.83 | WO | 2006/089178 | 8/2006 |
| 2006/0271098 A1 | 11/2006 | Peacock, III ................ 606/200 | WO | 2006/104591 | 10/2006 |
| 2007/0006441 A1 | 1/2007 | McNiven et al. ............. 29/508 | WO | 2006/105065 | 10/2006 |
| 2007/0016132 A1 | 1/2007 | Oepen et al. ................ 604/96.01 | WO | 2006/116636 | 11/2006 |
| 2007/0016165 A1 | 1/2007 | Von Oepen et al. .......... 604/525 | WO | 2006/127929 | 11/2006 |
| 2007/0021771 A1 | 1/2007 | Oepen et al. ................ 606/194 | WO | 2007/035865 | 3/2007 |
| 2007/0055365 A1 | 3/2007 | Greenberg et al. .......... 623/1.44 | WO | 2007/035885 | 3/2007 |
| 2007/0060942 A2 | 3/2007 | Zadno-Azizi ................ 606/194 | | | |
| 2007/0065484 A1 | 3/2007 | Chudzik et al. ............... 424/426 | | | |
| 2007/0083188 A1 | 4/2007 | Grandt et al. ................ 604/524 | | | |
| 2007/0123838 A1 | 5/2007 | Bernard et al. ................ 604/500 | | | |
| 2007/0129752 A1 | 6/2007 | Webler et al. ................ 606/200 | | | |
| 2007/0204455 A1 | 9/2007 | Knott et al. ................ 29/508 | | | |
| 2007/0244503 A1 | 10/2007 | Casey et al. ................ 606/200 | | | |
| 2008/0051671 A1 | 2/2008 | Broome et al. ............... 600/504 | | | |

FOREIGN PATENT DOCUMENTS

| | | |
|---|---|---|
| WO | 98/46297 | 10/1998 |
| WO | 99/65420 | 12/1999 |

OTHER PUBLICATIONS

Written Opinion, pp. 1-7 (Mar. 30, 2009).

Decousus, Herve, et al., "A Clinical Trial of Vena Caval Filters in the Prevention of Pulmonary Embolism in Patients with Proximal Deep-Vein Thrombisis", *The New England Journal of Medicine*, vol. 338, No. 7, pp. 409-415 (Feb. 12, 1998).

Lin, Peter H., et al., "Vena Caval Filters in the Treatment of Acute DVT", *Endovascular Today*, pp. 40-50 (Jan. 2005).

\* cited by examiner

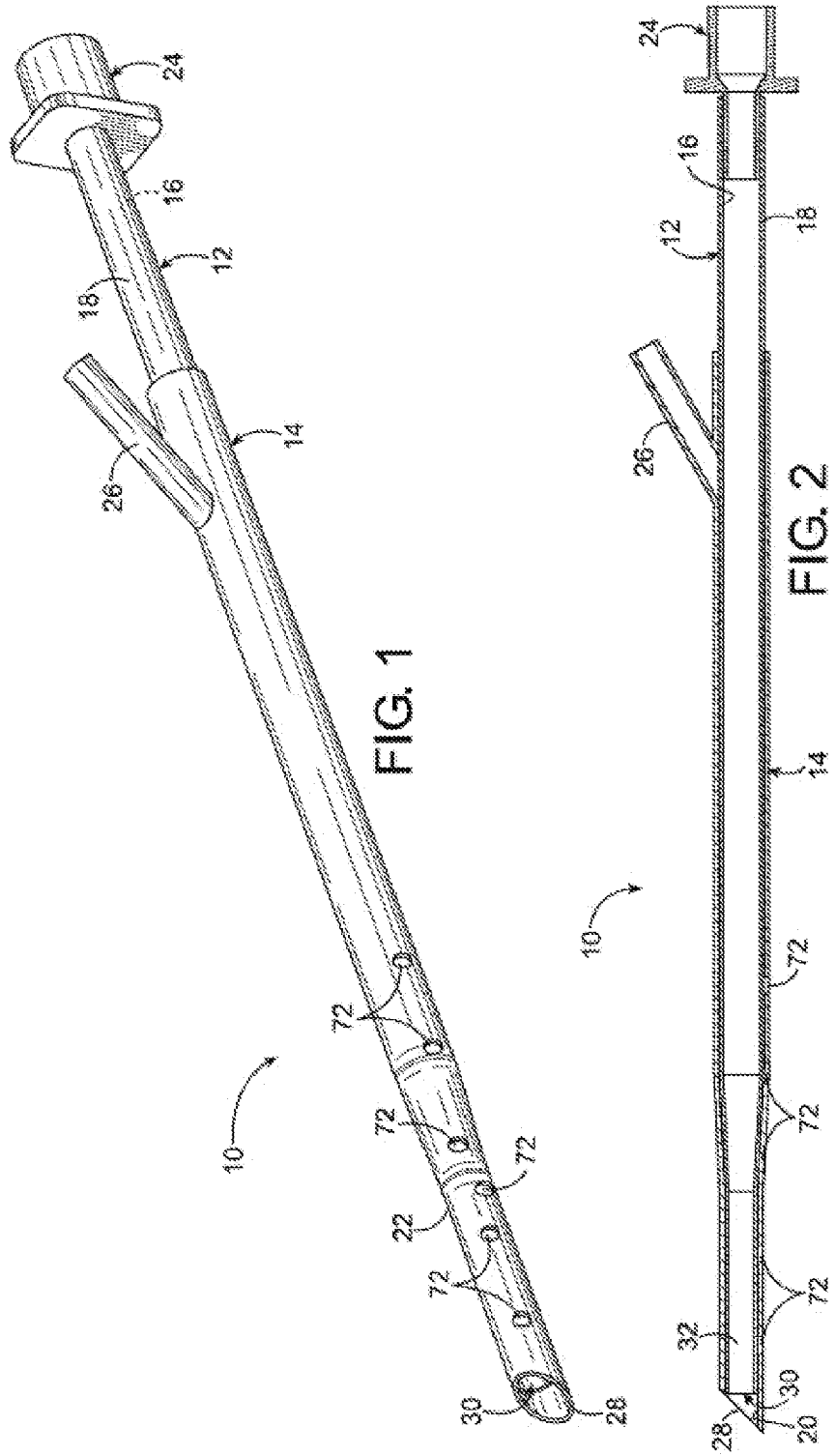

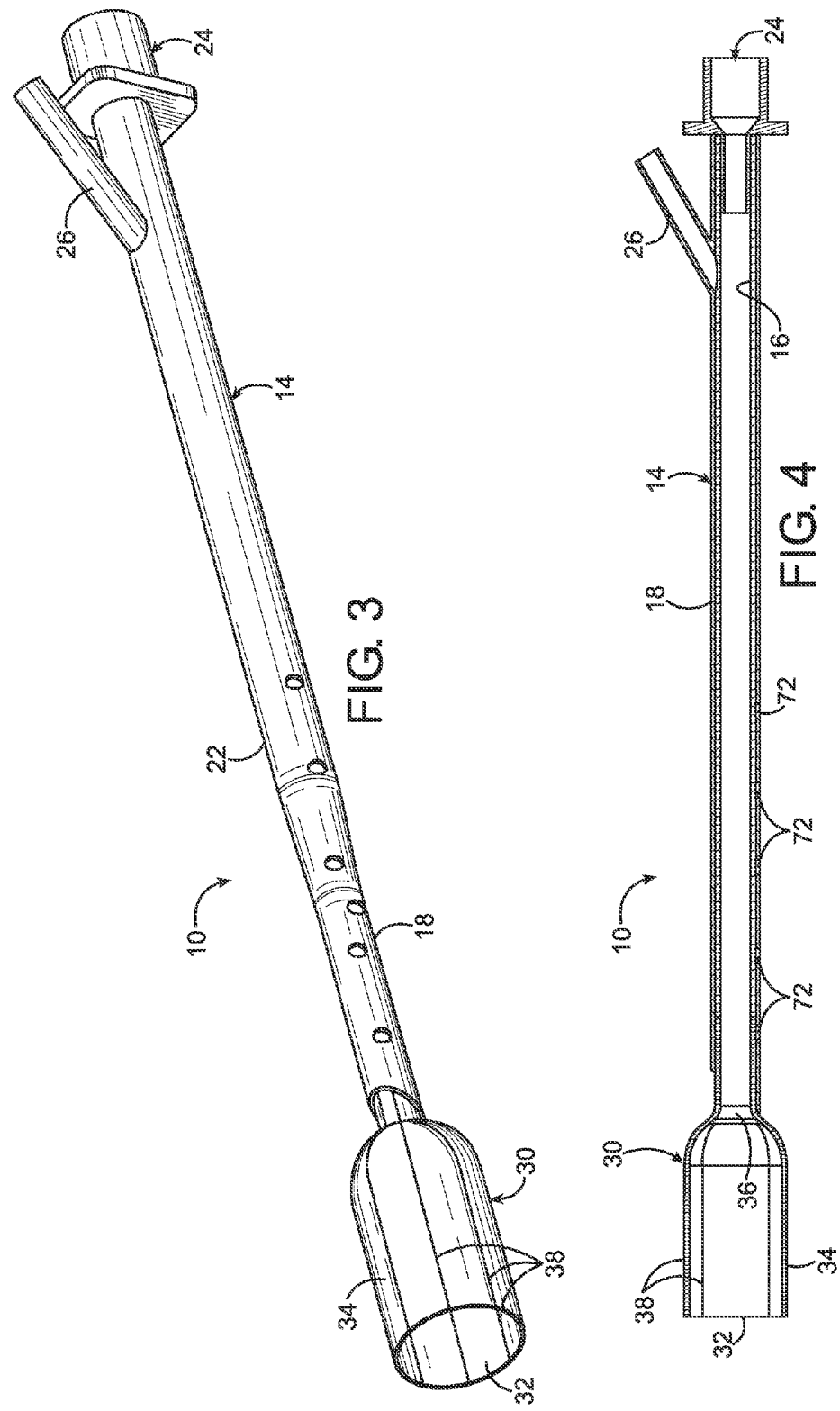

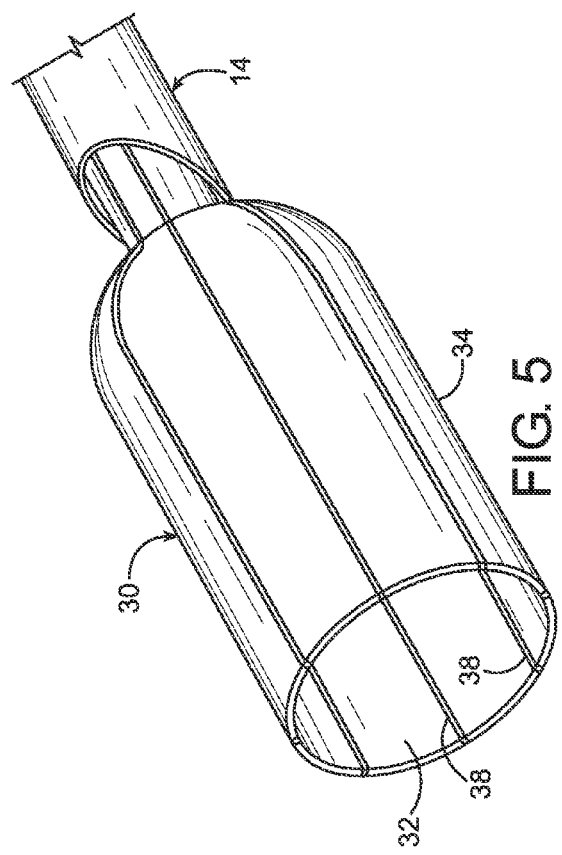
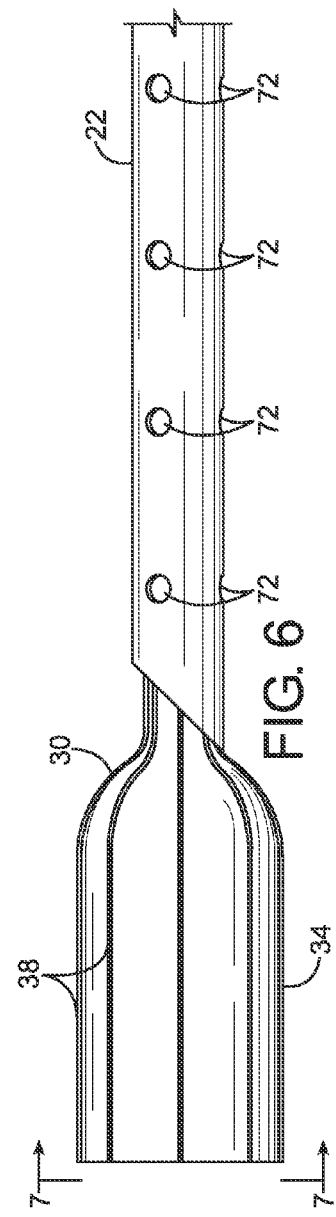
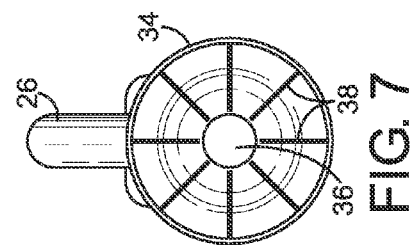

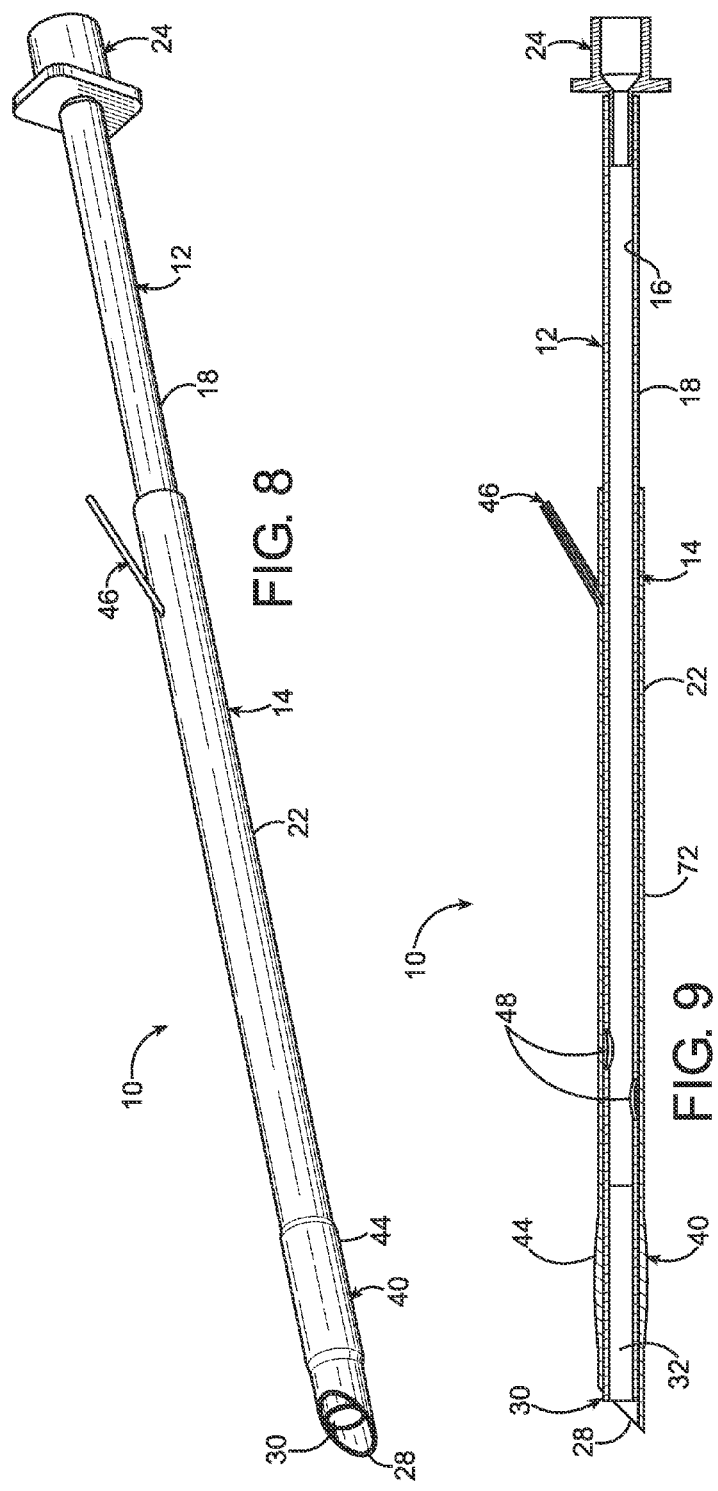

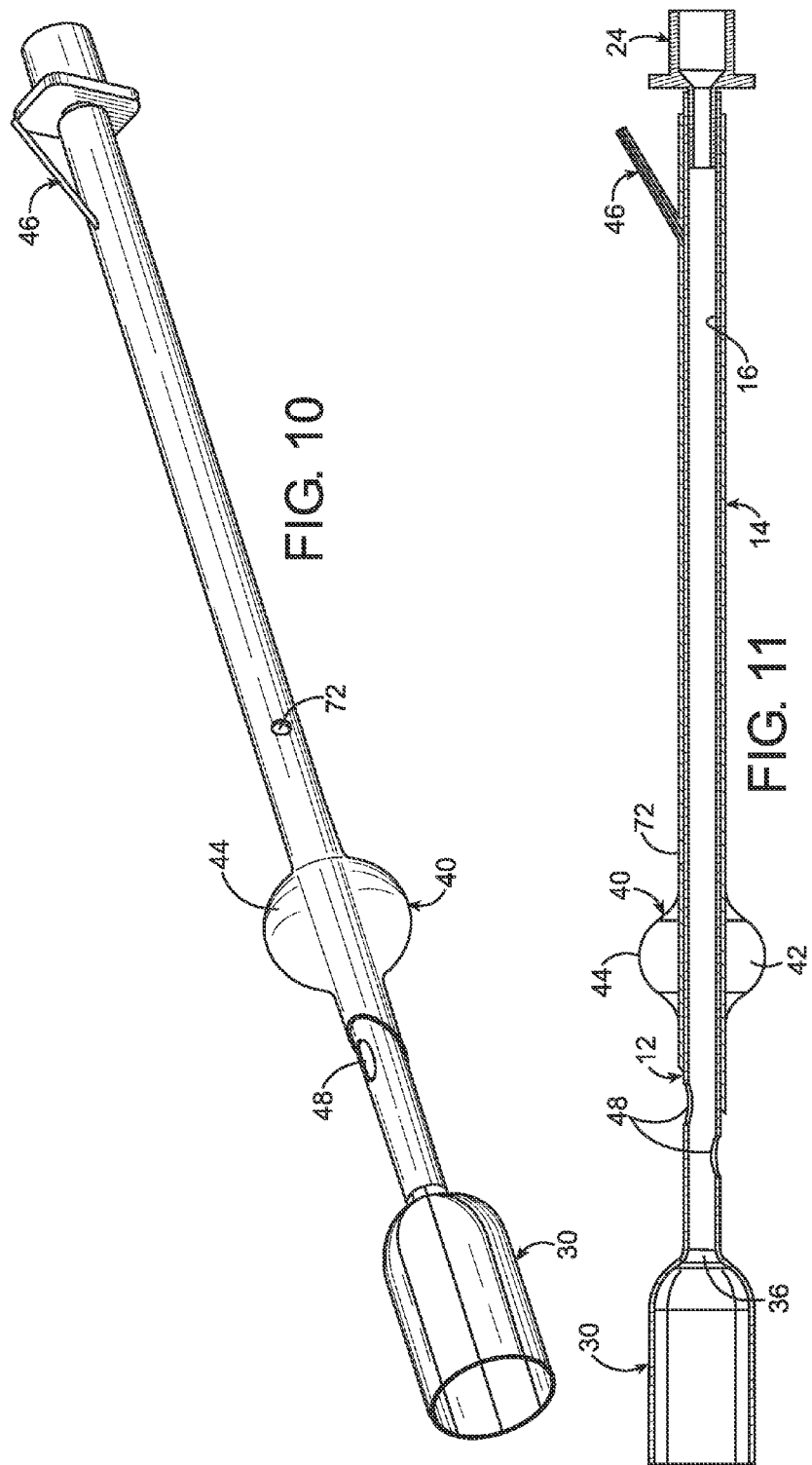

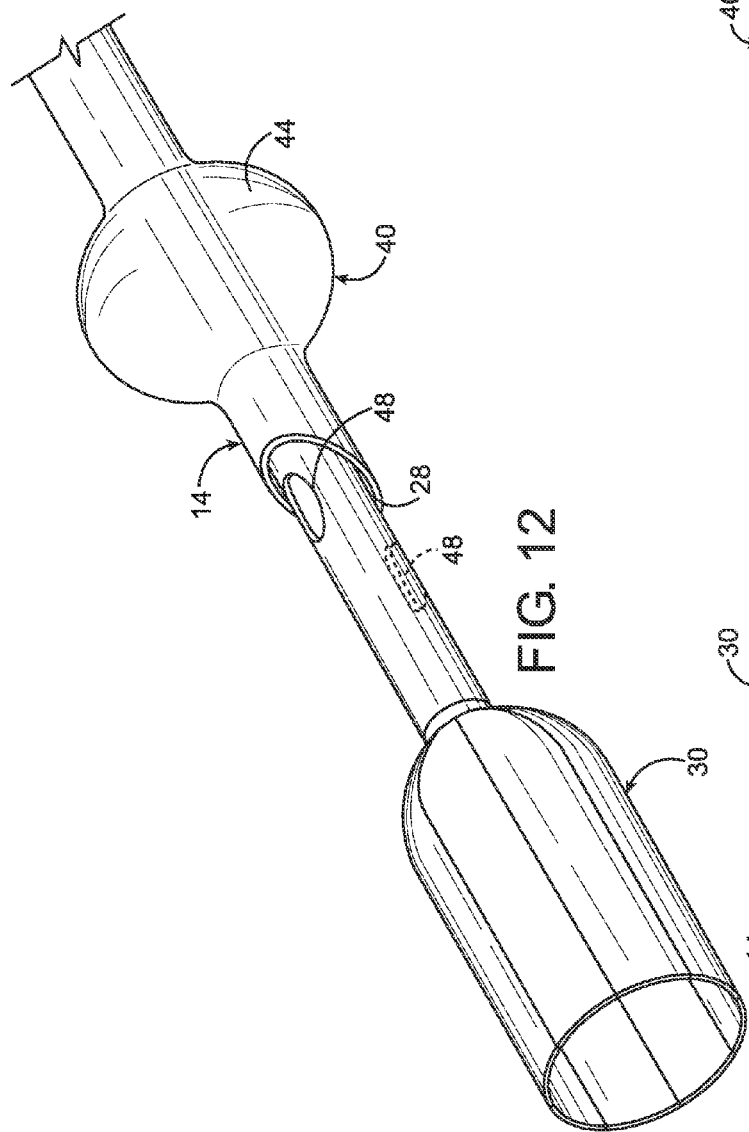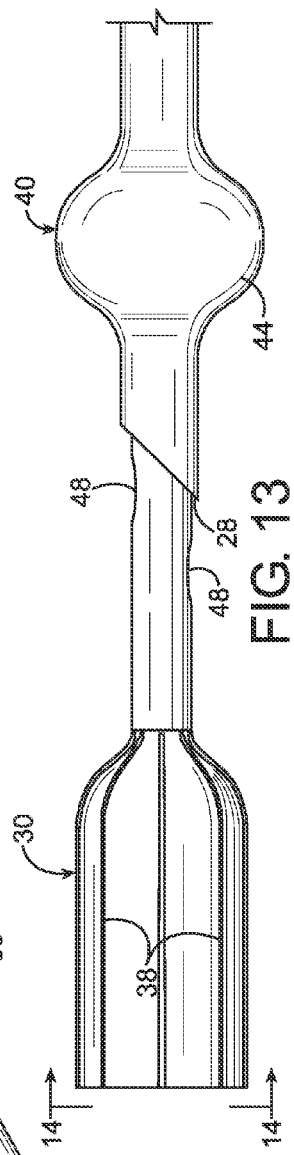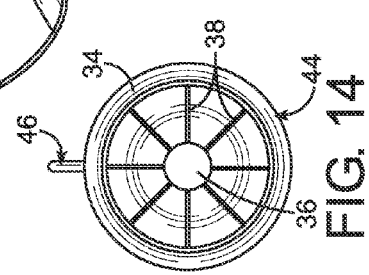

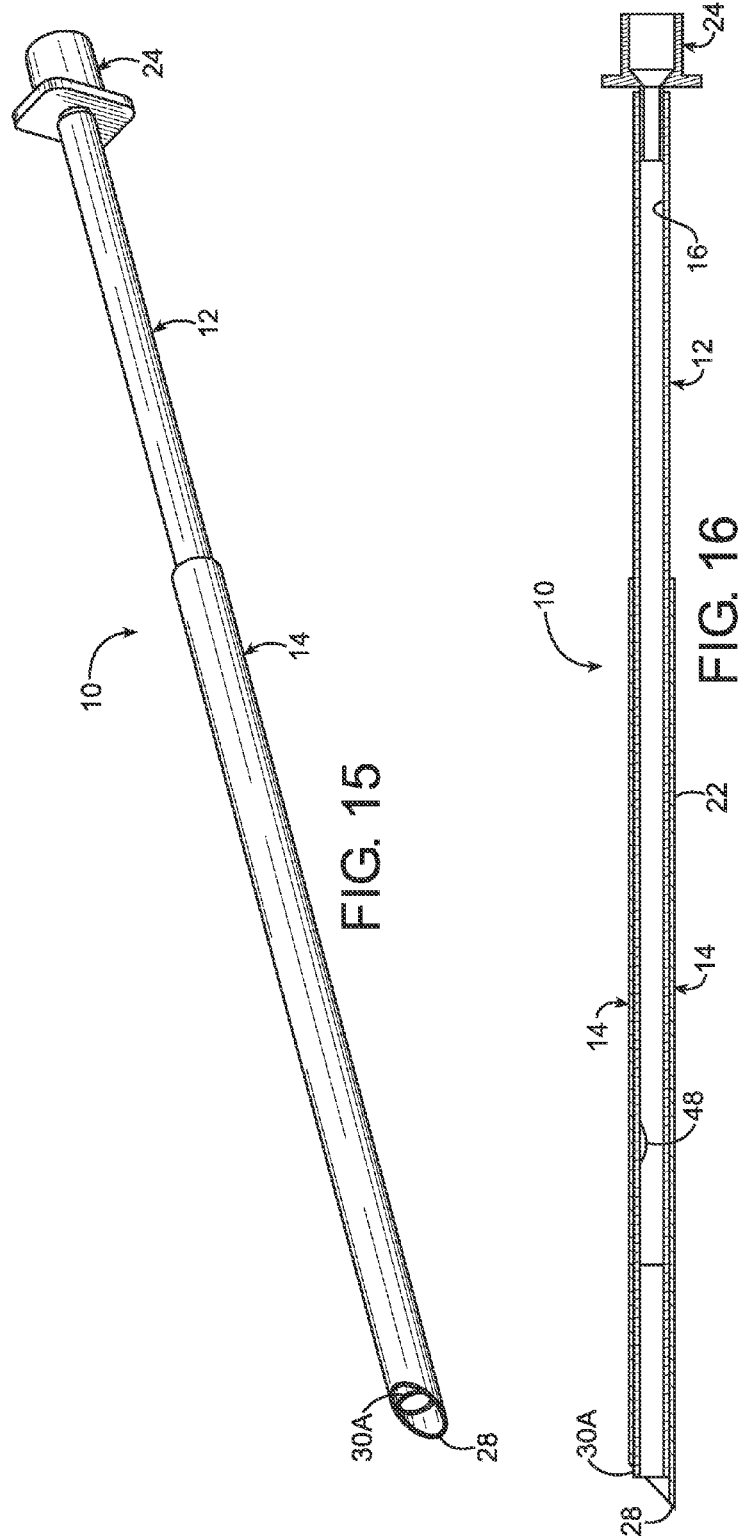

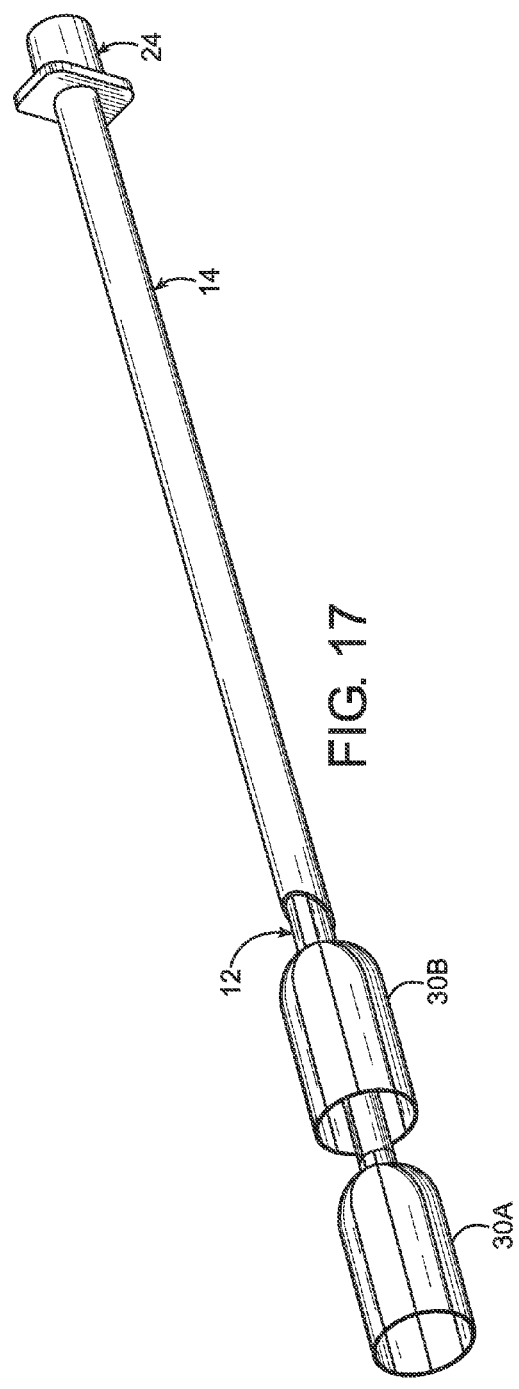
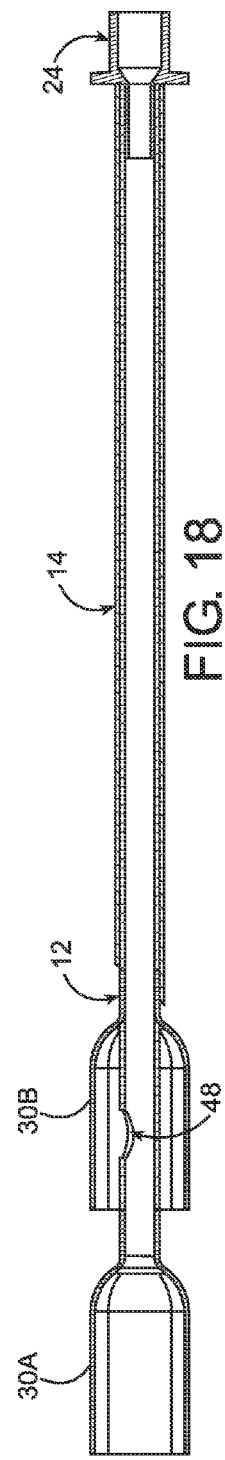

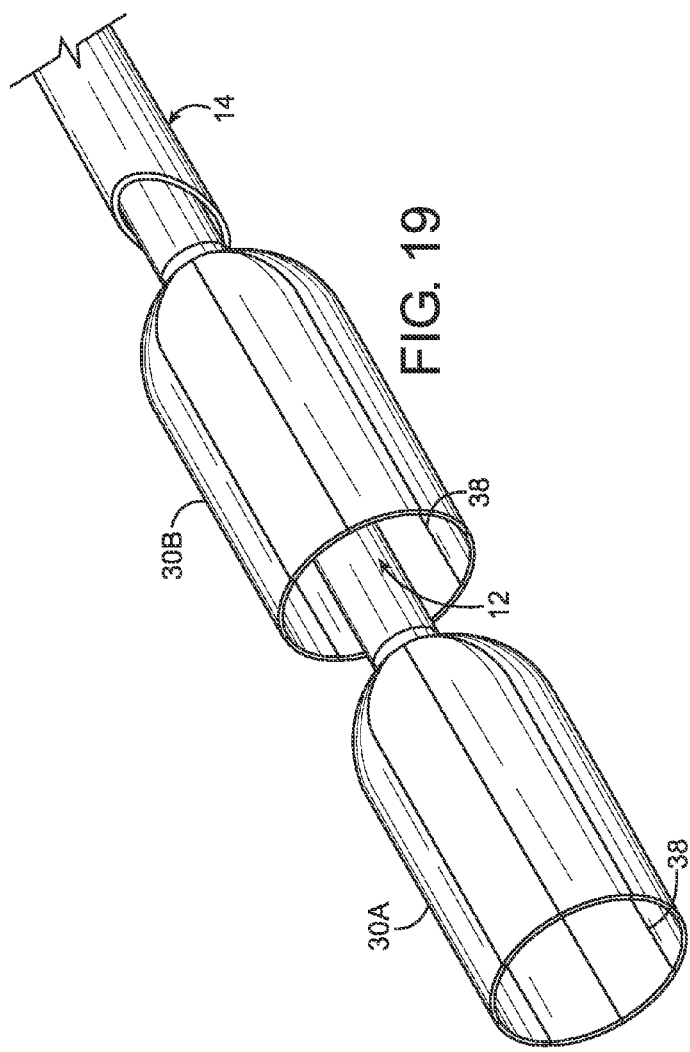
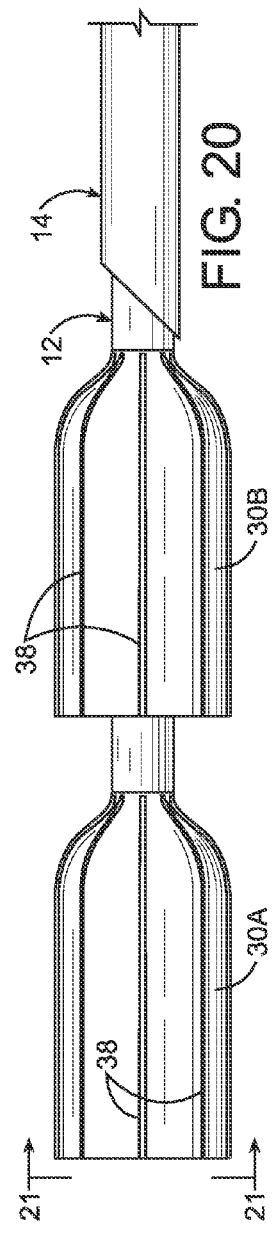
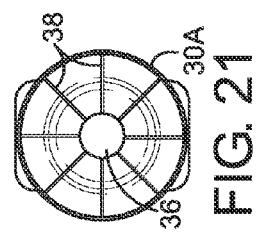

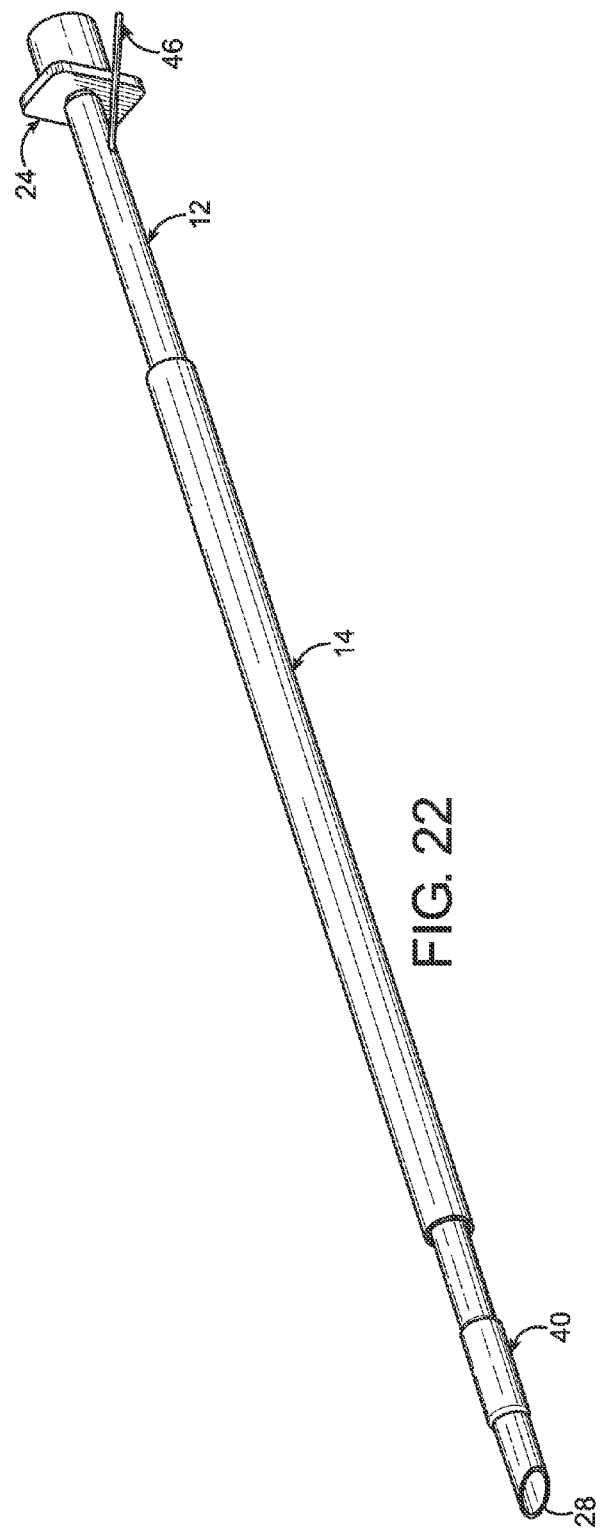
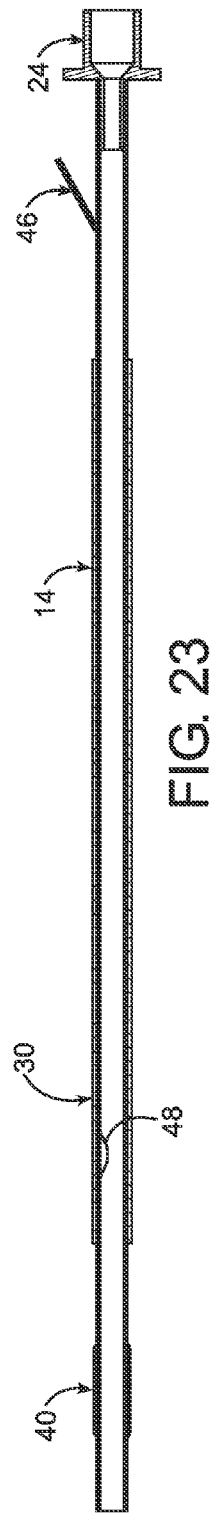
FIG. 22
FIG. 23

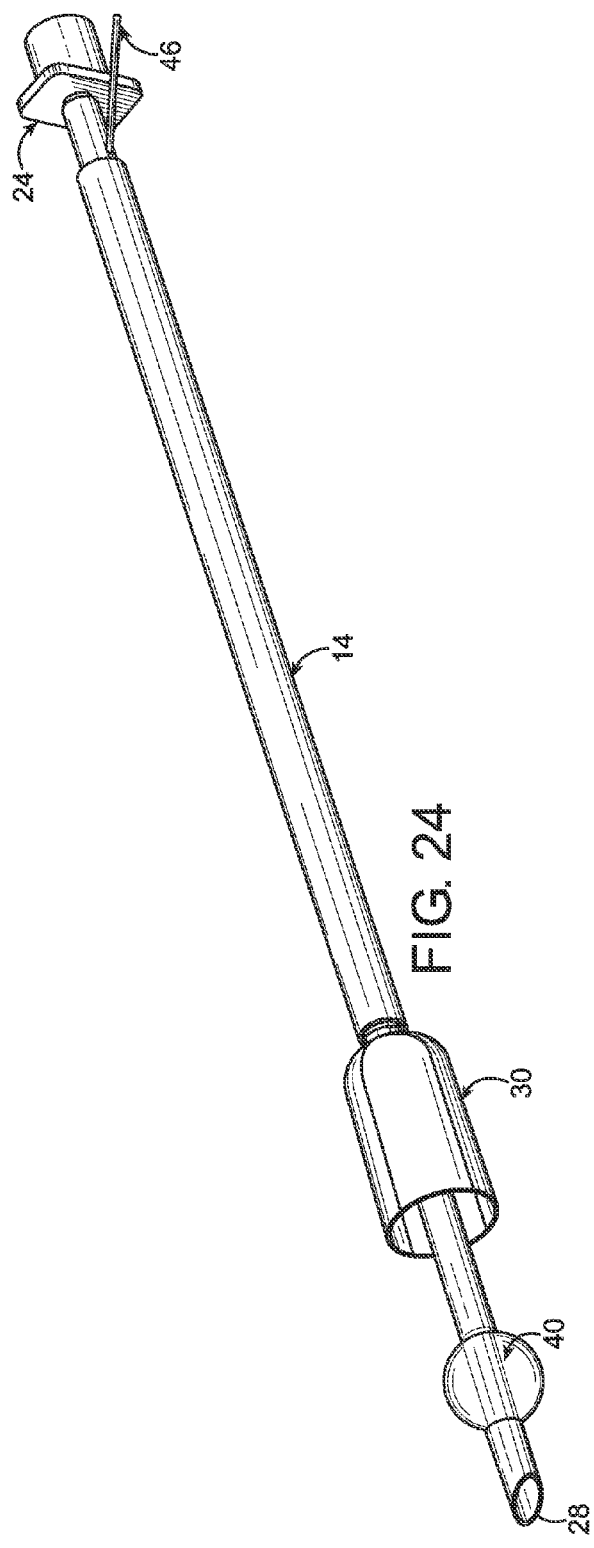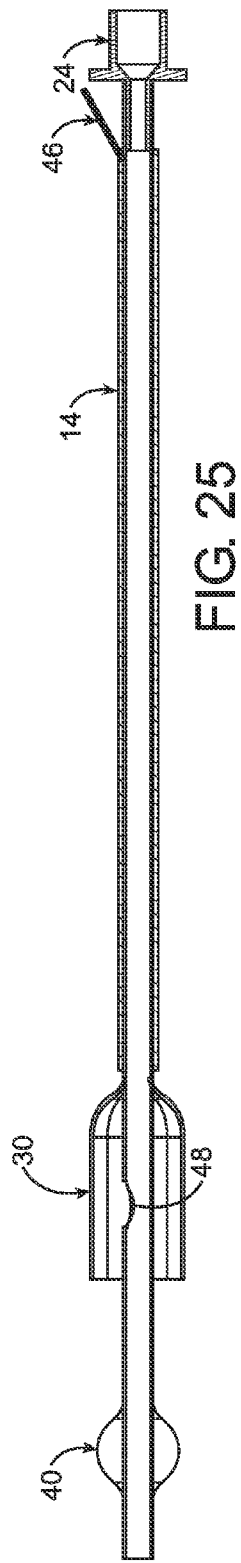

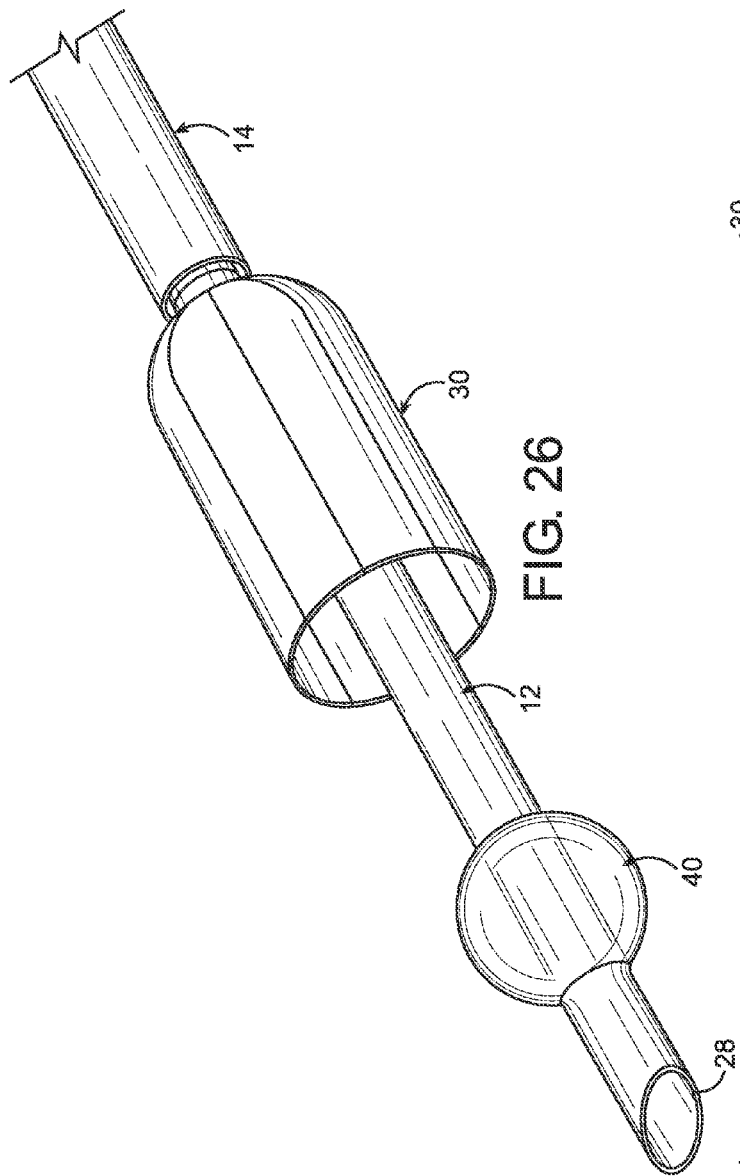
FIG. 26
FIG. 27
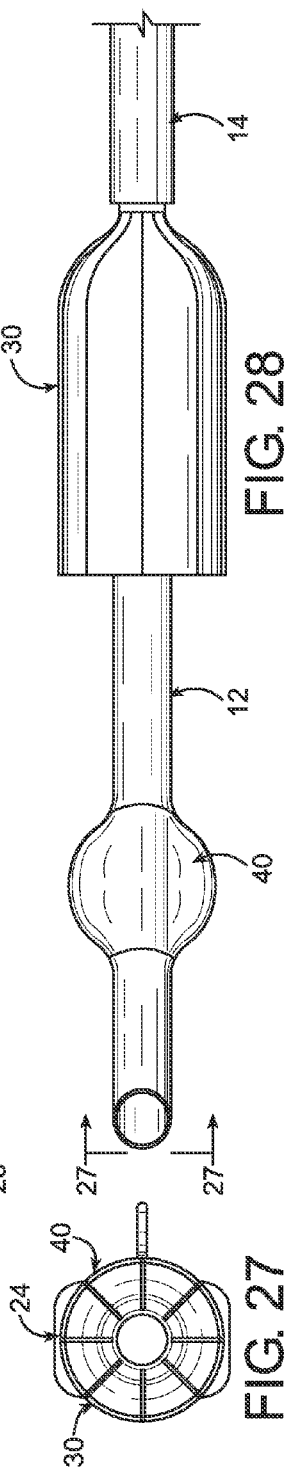
FIG. 28

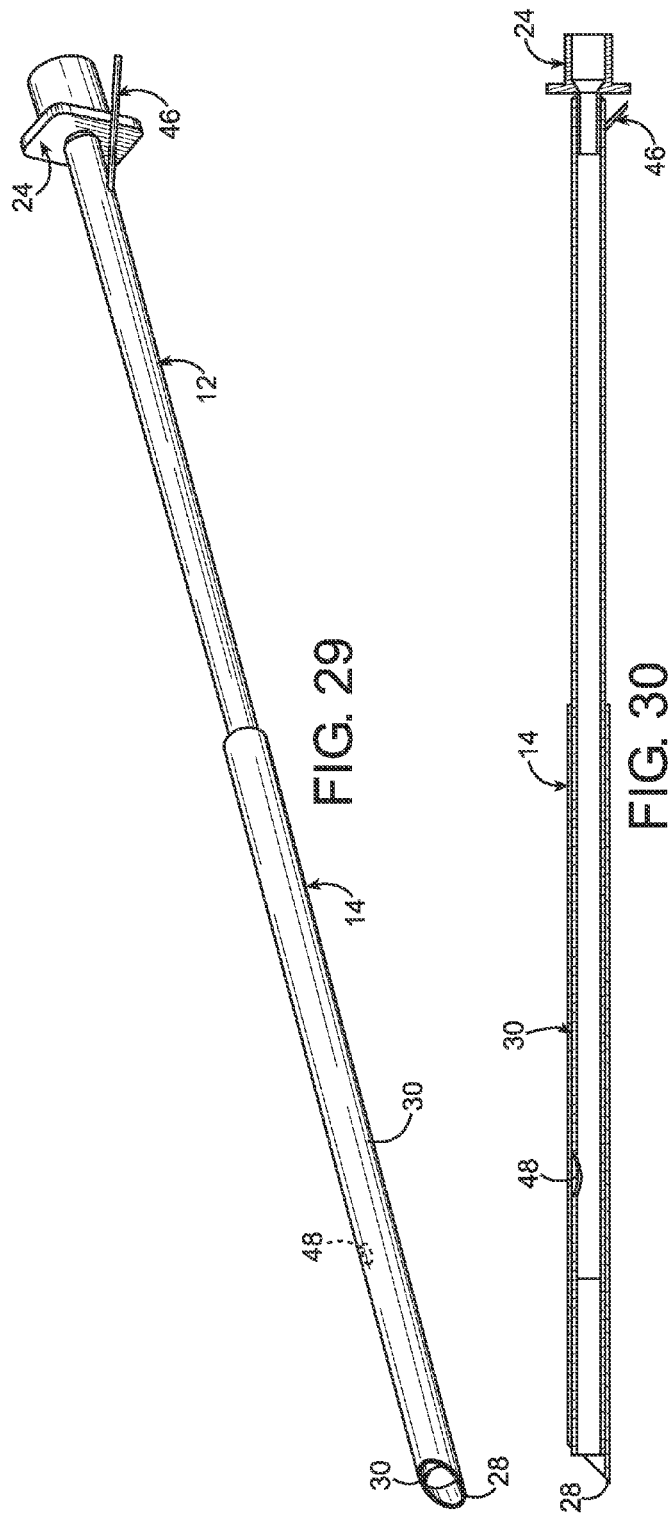

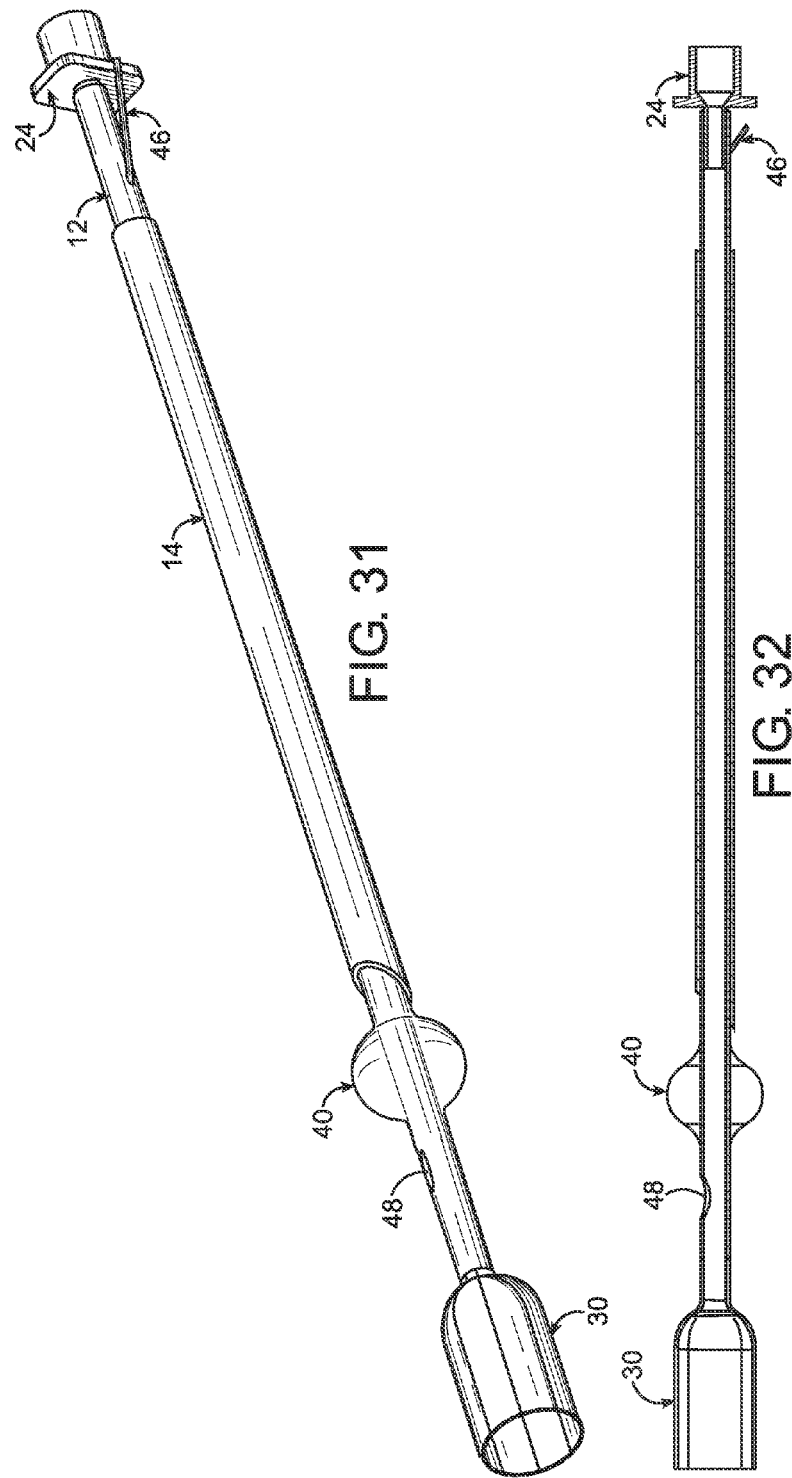

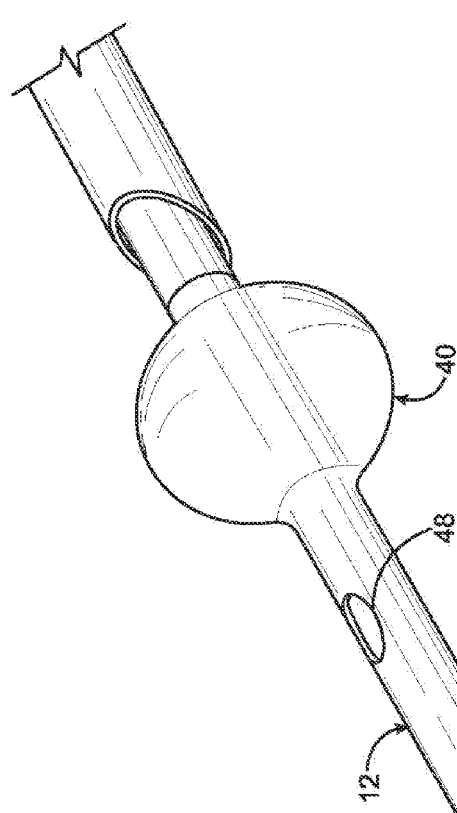
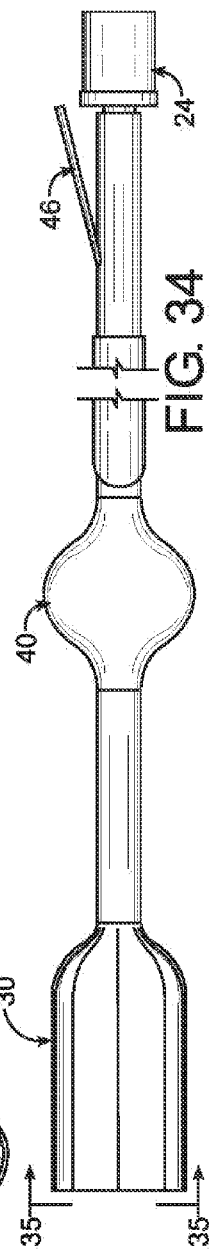
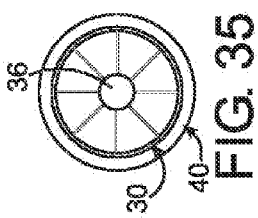

AIRWAY ASSEMBLY AND METHODS OF USING AN AIRWAY ASSEMBLY

REFERENCE TO RELATED APPLICATIONS

This case is a continuation-in-part of U.S. patent application Ser. No. 10/569,397 filed on Nov. 13, 2006 and published on Mar. 8, 2007 as US-2007-0055343-A1, which claims priority to PCT Application No. PCT/US04/027285, filed Aug. 23, 2004, which claims priority from U.S. Provisional Application No. 60/497,140, filed Aug. 22, 2003.

BACKGROUND

Embodiments described herein generally relate to an airway assembly and methods of using an airway assembly. More specifically, embodiments described herein relate to devices for endotracheal intubation and methods of performing endotracheal intubation. Tracheal intubation is a common and routine procedure for restoring or for maintaining the air passageway to ventilate the lungs by allowing for externally applied or artificial respiration when the patient is unable to breath. Endotracheal intubation is a procedure by which an endotracheal tube is inserted through the mouth into the trachea. Before surgery, this is often done under deep sedation. In emergency situations, the patient is often unconscious at the time of this procedure. Often, endotracheal intubation is used when patients are critically ill and cannot maintain adequate respiratory function to meet their needs.

Conventional endotracheal tubes consist generally of a semi-rigid flexible plastic tube having a beveled distal end, a ventilator connector at a proximal end for connecting an external ventilator to the endotracheal tube, a dilatable balloon positioned proximate the distal end of the tube and, coupled to an outer wall surface of the tube, an inflation tube or lumen associated with the tube wall that communicates air to the balloon to inflate the balloon and seat the balloon, and, hence, the tube, within the trachea and seal the trachea to prevent backflow of air.

Usually, an endotracheal tube is inserted using a laryngoscope that permits visualization of the vocal cords and the upper portion of the trachea and retracts the tongue during intubation. Proper intubation is critical in order to ventilate the lungs. If the tube is inadvertently placed in the esophagus, adequate lung ventilation will not occur, with possible concomitant neural injury, cardiac arrest or death. Aspiration of stomach contents can result in pneumonia and acute respiratory distress syndrome. Placement of the tube too deep can result in only one lung being ventilated and can result in a pneumothorax as well as inadequate ventilation. During endotracheal tube placement, damage can occur to the teeth, to the soft tissues in the back of the throat, as well as to the vocal cords.

Assuming that an endotracheal tube is placed properly and is secured within the trachea by an inflated balloon, the endotracheal tube provides a good air passageway to ventilate the lungs, however, having an endotracheal tube residing within the trachea implies several changes to the patient's airways. An important change when a patient is intubated is that the airway passages loses sterility and becomes colonized within a few hours of starting mechanical ventilation with a risk of ventilator associated pneumonia—around 8% to 28% of patients admitted in the intensive care unit. The risk for developing pneumonia has been clinically demonstrated to be associated with the current endotracheal tubes. Pneumonia is often the result of aspiration during intubation secondary to the large size of the endotracheal tubes being introduced through the narrow vocal cord space, contaminated secretions pooling above the endotracheal tube cuff or secretions leaking around the cuff. Leakage around an endotracheal cuff is commonly associated with a decreased pressure inside the cuff which occurs a few hours post-inflation and the resultant formation of creases or channels in the partially deflated cuff that allow contaminated secretions to pass into the more distal bronchial passages. Finally, pneumonia may occur due to decreased clearance of mucus produced by the lungs. Decreased mucus clearance frequently occurs in patients requiring mechanical ventilation due to the position of the tube in the middle of the trachea such that distal secretions are not removed by patient coughing but are only removed by a suction catheter advanced into the distal bronchial passages through the endotracheal tube. There are other drawbacks presented by currently available endotracheal tubes, specially related to the pressure transmitted from the cuff to the tracheal mucosa. This has been associated with post-intubation tracheal narrowing or stenosis which is a very serious complication with devastating implications for patients and requiring a very complex surgical management that is performed in few specialized centers. Accordingly, it is desirable to improve endotracheal tubes.

SUMMARY

Many embodiments of an airway assembly and methods of using an airway assembly are disclosed. In one embodiment, an airway assembly includes an outer tube, an inner tube disposed coaxially and reciprocally moveable within the outer tube, and a seal disposed on the inner tube. The seal is diametrically movable between a collapsed position in which the seal is constrained by the outer tube and an expanded position where the seal is released from the outer tube and engages an airway, such as a tracheal or a bronchial passage.

Another embodiment is an airway assembly that includes an outer tube having a proximal portion and a distal portion, and an inner tube disposed coaxially and reciprocally moveable within the outer tube. The inner tube has a proximal portion and a distal portion. The proximal portion of the outer tube has an outer diameter that is larger than an outer diameter of the distal portion of the outer tube. The proximal portion of the inner tube has an outer diameter that is larger than an outer diameter of the distal portion of the inner tube.

A further embodiment provides a method of using an airway assembly in an airway. The method comprises the steps of: providing an airway assembly having an outer tube, an inner tube disposed coaxially and reciprocally movable within the outer tube, and a diametrically expandable seal disposed on the inner tube. The seal is inserted into the airway. The seal is moved from a constrained collapsed position to an expanded position where the seal engages the airway. Fluid is moved through the inner tube and the seal.

An additional embodiment provides a method of using an airway assembly in an airway. The method comprises the steps of: providing an airway assembly having an outer tube, and an inner tube disposed coaxially and reciprocally moveable within the outer tube. The airway assembly is placed in a first status. The airway assembly is inserted into an airway when the airway assembly is in the first status. The outer tube is moved with respect to the inner tube to place the airway assembly in a second status. The outer tube is moved with respect to the inner tube to place the airway assembly in a third status.

DESCRIPTION OF THE DRAWINGS

FIG. 1 is a perspective view of an airway assembly described herein in a collapsed configuration;

FIG. 2 is a side-elevational sectional view of the airway assembly of FIG. 1;

FIG. 3 is a perspective view of an airway assembly of FIG. 1 in an expanded configuration;

FIG. 4 is a side-elevational sectional view of the airway assembly of FIG. 3;

FIG. 5 is an enlarged view of a portion of the airway assembly of FIG. 3;

FIG. 6 is an elevational view of portions of the airway assembly of FIG. 3;

FIG. 7 is an end view, taken along line 7-7 of FIG. 6;

FIG. 8 is a perspective view of an airway assembly described herein in a collapsed configuration;

FIG. 9 is a side-elevational sectional view of the airway assembly of FIG. 8;

FIG. 10 is a perspective view of the airway assembly of FIG. 8 in an expanded configuration;

FIG. 11 is a side-elevational sectional view of the airway assembly of FIG. 10;

FIG. 12 is an enlarged view of a portion of the airway assembly of FIG. 10;

FIG. 13 is an side-elevational view of a portion of the airway assembly of FIG. 12;

FIG. 14 is an end view, taken along line 14-14 of FIG. 13;

FIG. 15 is a perspective view of an airway assembly described herein in a collapsed configuration;

FIG. 16 is a side-elevational sectional view of the airway assembly of FIG. 15;

FIG. 17 is a perspective view of the airway assembly of FIG. 15 in an expanded configuration;

FIG. 18 is a side-elevational sectional view of the airway assembly of FIG. 17;

FIG. 19 is an enlarged view of a portion of the airway assembly of FIG. 17;

FIG. 20 is an elevational view of a portion of the airway assembly of FIG. 19;

FIG. 21 is an end view taken along line 21-21 of FIG. 20;

FIG. 22 is a perspective view of an airway assembly described herein in a collapsed configuration;

FIG. 23 is a side-elevational sectional view of the airway assembly of FIG. 22;

FIG. 24 is a perspective view of the airway assembly of FIG. 22 in an expanded configuration;

FIG. 25 is a side-elevational sectional view of the airway assembly of FIG. 24;

FIG. 26 is an enlarged view of a portion of the airway assembly of FIG. 24;

FIG. 27 is an end view taken along line 27-27 of FIG. 28;

FIG. 28 is an elevational view of a portion of the airway assembly of FIG. 26;

FIG. 29 is a perspective view of an airway assembly described herein in a collapsed configuration;

FIG. 30 is a side-elevational sectional view of the airway assembly of FIG. 29;

FIG. 31 is a perspective view of the airway assembly of FIG. 29 in an expanded configuration;

FIG. 32 is a side-elevational sectional view of the airway assembly of FIG. 31;

FIG. 33 is an enlarged view of a portion of the airway assembly of FIG. 31;

FIG. 34 is an elevational view of a portion of the airway assembly of FIG. 31;

FIG. 35 is an end view taken along line 35-35 of FIG. 34;

DETAILED DESCRIPTION OF THE PREFERRED EMBODIMENTS

Figure 36:
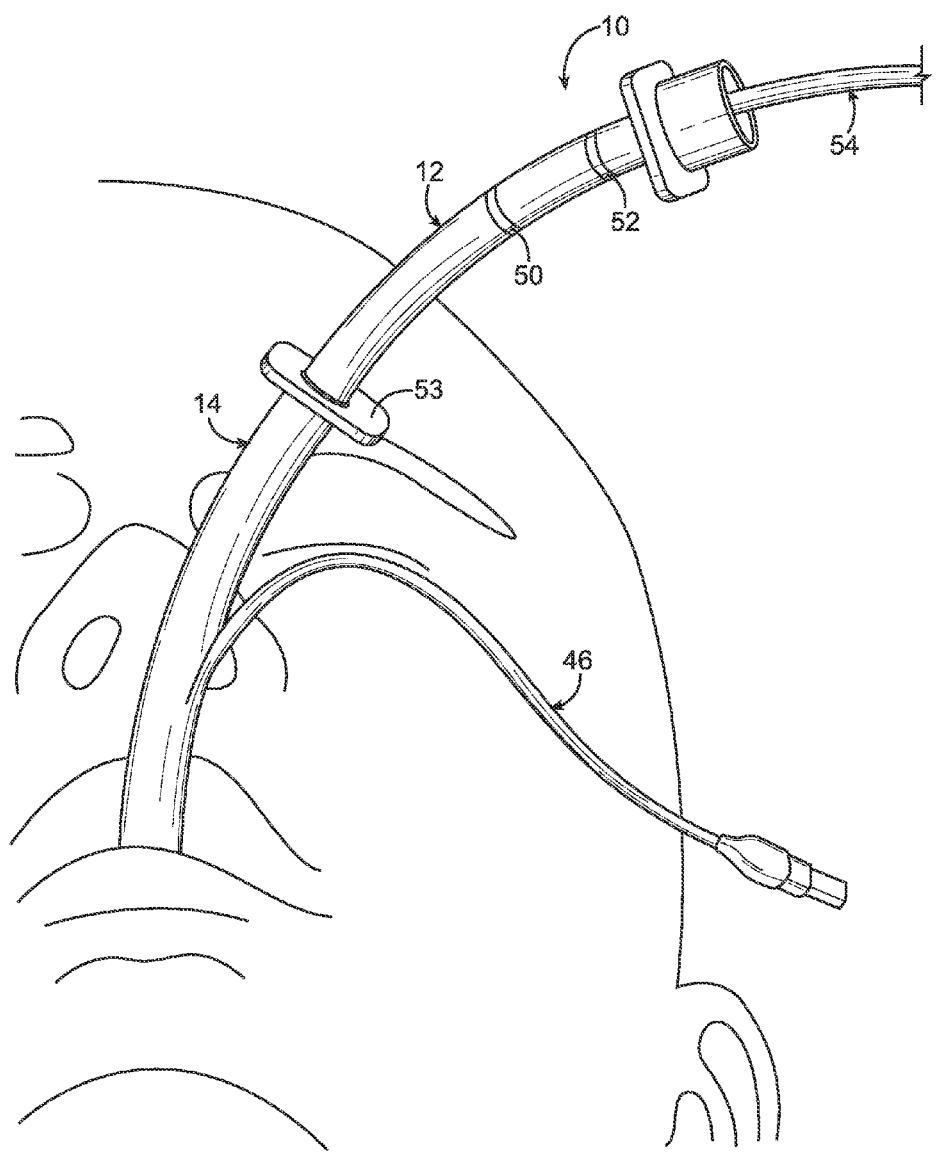
FIG. 36 is a diagrammatic view of a portion of an airway assembly described herein used with a patient.

Embodiments described here relate generally to an airway assembly 10. The airway assembly 10 can be used to intubate a patient. Structures common to the embodiments are provided with like reference numerals. As the embodiments are related, features, such as dimensions, materials and the like, may be shared. Differences among the embodiments are highlighted when present. Both structures of and methods of use of the embodiments are described below. Some features of the embodiments may become clear after consideration of the entirety of this description.

One embodiment of an airway assembly 10 is shown in FIG. 1. This embodiment is similar to the airway assembly disclosed in co-pending PCT patent application International Publication Number WO 2005/018713 which is assigned to the assignee of the present case. The disclosure of that PCT patent application is incorporated herein in its entirety.

Many embodiments of an airway assembly and methods of using an airway assembly are disclosed. In one embodiment, an airway assembly includes an outer tube, an inner tube disposed coaxially with the outer tube, and a seal disposed on the inner tube. The seal is movable between a collapsed position and an expanded position where the seal engages an airway. Another embodiment is an airway assembly that includes an outer tube having a proximal portion and a distal portion, and an inner tube disposed coaxially with the outer tube. The inner tube has a proximal portion and a distal portion. The proximal portion of the outer tube has an outer diameter that is larger than an outer diameter of the distal portion of the outer tube. The proximal portion of the inner tube has an outer diameter that is larger than an outer diameter of the distal portion of the inner tube. A further embodiment provides a method of using an airway assembly in an airway. The method comprises the steps of: providing an airway assembly having an outer tube, an inner tube disposed coaxially with the outer tube, and a seal disposed on the inner tube. The seal is inserted into the airway. The seal is moved from a collapsed position to an expanded position where the seal engages the airway. Fluid is moved through the inner tube and the seal. An additional embodiment provides a method of using an airway assembly in an airway. The method comprises the steps of: providing an airway assembly having an outer tube, and an inner tube disposed coaxially with the outer tube. The airway assembly is placed in a first status. The airway assembly is inserted into an airway when the airway assembly is in the first status. The outer tube is moved with respect to the inner tube to place the airway assembly in a second status. The outer tube is moved with respect to the inner tube to place the airway assembly in a third status.

Drawing attention to FIGS. 1 and 2, the airway assembly 10 comprises an inner tube 12 having a central lumen, an inner surface 16 and an outer surface 18, an outer tube 14 having a central lumen, having an inner surface 20 and an outer surface 22 and a diametrically expansive seal 30. The inner tube 12 is disposed coaxially and reciprocally moveable within the outer tube 14. There is sufficient clearance provided between the inner surface 20 of the outer tube 14 and the outer surface 18 of the inner tube 12 to permit movement of the inner tube 12 with respect to the outer tube 14. A connector 24 is joined to the inner tube 12, at a proximal end thereof, so that a fluid, such as a gas, a liquid and the like, can flow between the connector 24 and the inner tube 12. Typically, a ventilator (not shown) is connected to connector 24 to provide an airflow to the patient. A distal end 28 of the inner tube 12 opposite to the proximal end thereof joined to the connector 24 is open to permit flow of fluid through the inner tube 12. A port 26 is formed on the outer tube 14 so that fluid may flow between the port 26 and a space between the outer surface 18 of the inner tube 12 and the inner surface 20 of the outer tube 14. In some embodiments, at least one perforation 72 is disposed on the outer tube 14. The at least one perforation 72 passes between the inner surface 20 and the outer surface 22 of the outer tube 14. The at least one perforation 72 allows for secretions collecting in the area above the diametrically expansive seal 30 to flow and be aspirated from an airway, it also allows for drug infusion or the like, between the outer tube 14 and the airway. The at least one perforation 72 may be positioned about 2 cm from the distal end 28 of the outer tube 14 and may be of any suitable shape, such as oblong, circular and the like, and any suitable size. Further, more than one perforation 72 may be included, and the more than one perforation 72 may be distributed along the length of the outer tube 14 in any desired manner.

Distal end 28 of the outer tube 14 is configured to facilitate introduction of the airway assembly 10 to a patient. The distal end 28 may have a bevel to facilitate passage through the vocal chords. Distal end 28 may also have a tapered diametric profile along its length, within the range of about 5 cm to about 7 cm in length, of a distal section of outer tube 14. This distal taper may also be collapsible and allows for easier visualization during the intubation procedure. In some embodiments, the outer diameter of the outer tube 14 is substantially within the range of about 10 mm to about 12 mm at its proximal end and can be reduced to an outer diameter substantially within the range of about 6 mm to about 8 mm at the distal end 28.

A diametrically expansive seal 30 is disposed at a distal end of the inner tube 12 opposite to the end thereof attached to the connector 24. There is a substantially smooth transition between the inner tube 12 and the expansive seal 30. The expansive seal 30 may comprise a generally tubular member having walls, a proximal end fixedly coupled to the inner tube 12, and an uncoupled distal end which opens distally to the anatomical airway. The proximal end of the seal is coupled to a distal end of the inner tube 12 and is in fluid flow communication with the central lumen of the inner tube 12. The walls and the distal end of the seal 30 may expand diametrically such that the distal end forms a diametrically enlarged distal opening sealingly seated against and in fluid flow communication with the airway. In some embodiments, the expansive seal 30 is movable between a diametrically collapsed position, shown in FIGS. 1 and 2, and a diametrically expanded position, shown in FIGS. 3 through 7. The expansive seal 30 has an inner surface 32 and an outer surface 34. The diametrically expansive seal 30 serves to seal the airway while exerting minimal pressure in the mucosa sufficient to prevent aspiration of secretions from the upper airways and trachea into the lungs, while preventing back leakage of air given during respiratory ventilation or while ventilating anesthesia gas.

The expansive seal 30 may have many appropriate dimensions in length, diameter, or in its general shape, all of which depend upon the patient criteria or the anatomy of the target airway, e.g., trachea or bronchus. For purposes of example, only, one set of dimensions are appropriate for pediatric patients and another set of dimensions are appropriate for a patient with a very large airways. In one embodiment, the expansive seal 30 has an expanded outer diameter of about 25 mm while, in another embodiment, the expansive seal 30 has an expanded outer diameter of about 20 mm. The outer diameter of expansive seal 30 may be within the range of about 18 to 20 mm for adult males and within the range of about 16 to 18 mm for adult females. It is understood by those skilled in the art that as one places the expansive seal 30 further distally within the bronchial branches, the anatomical diameter decreases, necessitating smaller diameter expansive seals 30. It is preferable, therefore, that the outer diameter of the expansive seal 30 be between about 10 to 25 mm in order to accommodate a wide variety of variances in anatomical structures of the trachea and bronchial branches.

An aperture 36 is on the expansive seal 30 adjacent the inner tube 12. The aperture 36 permits fluid flow through the inner surface 32 of the expansive seal 30. The aperture 36 is fluidly associated with the inner tube 12 to permit fluid flow between the inner tube 12 and the expansive seal 30.

The expansive seal 30 is preferably fabricated of a biocompatible material, such as silicone, which is suitable for use in the pulmonary system, particularly the trachea and bronchi. The expansive seal 30 may be fabricated using a single material, wherein the seal is formed as a single monolithic or unitary element, or of plural joined elements formed of the same biocompatible material. Alternatively, the expansive seal 30 may be fabricated of plural biocompatible materials may be joined as a composite. In either construct of the expansive seal 30, but more preferably, in the case of a composite construction of the expansive seal 30, at least one reinforcing member 38 is operably associated with the expansive seal 30 to facilitate movement of the expansive seal 30 between its diametrically collapsed and diametrically expanded positions. In accordance with the illustrated embodiments, plural reinforcing members 38 are associated with the expansive seal 30 and extend longitudinally along the expansive seal 30 in a radially spaced apart relationship relative to each other. The at least one reinforcing member 38 may be coupled to the expansive seal 30 on either its luminal or abluminal surfaces, or may be embedded within expansive seal 30 such that it resides at least partially within a wall thickness of the expansive seal 30. Alternatively, the at least one reinforcing member 38 may comprise a relatively thickened region, such as a rib or a pattern or ribs, of the same material employed in fabricating the expansive seal 30. The at least one reinforcing member 38 is preferably an elastic, shape memory or superelastic material, such as stainless steel, silicone, nitinol, chromium-molybdenum alloys, or similar materials. In this manner the expansive seal 30 is self-expanding upon being released from a constraining sheath or covering, such as the outer tube 14. For purposes of this application, when reference is made to expansive seal 30, such reference is intended to be inclusive of the at least one reinforcing member 38, where appropriate. Those of ordinary skill in the art will understand that the at least one reinforcing member 38 may or may not be necessary, depending upon the construction and materials employed in fabricating the expansive seal 30, in order to provide for either expansion or collapse, or to facilitate or aid in apposition or sealing of the expansive seal 30 against the anatomical airway.

When in its diametrically expanded position, the expansive seal 30 is intended to achieve the size of the airway while exerting low pressure against the tracheal wall, thereby inhibiting passage of secretions beyond the expansive seal 30 to areas of the airway beyond the expansive seal 30, and improving clearance from secretions deposited distal of the expansive seal 30. The expansive seal 30 also reduces the likelihood of unintended fluid passage through the airway. In some embodiments, the expansive seal 30 may include at least one radiopaque or fluoroscopic marker to facilitate imaging the position of the expansive seal 30 after placement. The expansive seal 30 may take on any appropriate shape, for instance, the expansive seal 30 can be substantially elongated, substantially rounded or substantially horseshoe shape in transverse cross section. In longitudinal aspect, expansive seal 30 preferably has an elongate generally tubular shape with a rounded taper at a proximal end thereof that connects with the distal end of the inner tube 12. The shape of the expansive seal 30 may be dictated by airway anatomy, by compatibility with the cough mechanism and by a need to reduce the likelihood of aspiration of secretions. In some embodiments, a distal portion of the expansive seal 30, sometimes measuring about 2 to about 3 mm in axial length, may be everted to afford a smoother circumferential surface area for tissue engagement. Everting a distal portion of the expansive seal 30 may reduce potential tissue growth around the expansive seal 30, and possibly facilitate advancement of the inner tube 12 with reduced risk of trauma to the patient.

Another embodiment of the airway assembly 10 is illustrated in FIGS. 8 through 14. As elements of this embodiment are substantially similar to elements of the embodiment shown in FIG. 1 through 7, like reference numerals are used for similar elements. The modifications in the airway assembly 10 are intended to provide independent ventilation to each one of the lungs as commonly required for surgical procedures such us lobectomies or in cases in which independent or single lung ventilation is desired. The following discussion highlights elements not previously emphasized.

The embodiments shown in FIGS. 8 through 14 include modifications to provide both single and double lung ventilation. An inflatable member 40, such as a balloon, is disposed proximate the distal end 28 of the outer tube 14. The inflatable member 40 has an inner surface 42 and an outer surface 44 and is movable between a deflated position, shown in FIGS. 8 and 9, and an inflated position shown in FIGS. 10 through 14. In one embodiment, the inflatable member 40 is intended to fully inflate at a pressure substantially within the range of about 15 to about 30 cm $H_2O$. At least one aperture 48 is disposed in the inner tube 12. It is preferable according to this embodiment to provide at least two apertures 48, as shown in FIGS. 9 and 11 to permit the ventilation fluid to have sufficient flow to the second lung. The at least one aperture 48 is movable between an open position and a closed position by axially moving the inner tube 12 relative to outer tube 14, the at least one aperture 48 is exposed to an open position or retracted within the outer tube 14 to a closed position. The at least one aperture 48 allows fluid movement through the aperture 48 and passing between the interior and exterior of the inner tube 12. However, it is to be noted that, because the inner tube 12 is moveable with respect to the outer tube 14, the tubes 12 and 14 may be positioned such that fluid flow through the at least one aperture 48 is restricted, i.e. the at least one aperture 48 is in a closed position. FIGS. 8 and 9 illustrate the relative position between inner tube 12 and outer tube 14 wherein the at least one aperture 48 is in the closed position within the outer tube 14. Hence, it is to be appreciated that fluid flow through the at least one aperture 48 is dependent upon relative position of the inner tube 12 and the outer tube 14. It is to be noted that while the Figures show that the inflatable member 40 is in its inflated position when the expansive seal 30 is in its expanded position, and the inflatable member 40 is in its deflated position when the expansive seal 30 is in its collapsed position, this does not always have to be the case. For example, the inflatable member 40 may be in its deflated position when the expansive seal 30 is in its expanded position or the inflatable member 40 may be in its inflated position while expansive seal 30 is in its collapsed position.

An inflation port 46 is disposed in communication with the outer tube 14 and communicates with the inner surface 42 of the inflatable member 40 so that fluid can flow between the port 46 and the inflatable member 40. A suitable conduit, not shown for clarity, is disposed on or in the outer tube 14 for conveying an inflation fluid between the inflation port 46 and the inflatable member 40. In this manner, this fluid flow controls inflation or deflation of the inflatable member 40 between its inflated and deflated positions. Once the endotracheal tube is placed such that the distal end of the inner tube 12 is positioned at a desired location in the right or left bronchus, the outer tube 14 is retracted to release the expansive seal 30 permitting expansive seal 30 to diametrically expand and sealingly conform against the bronchus. The outer tube 14 is retracted sufficiently to position the inflation member 40 at a desired location within the trachea and inflated into sealing conformity against the trachea. If the apertures 48 are exposed, ventilation will occur to both lungs, with one lung being ventilated through the expansive seal 30 and the other lung being ventilated through the apertures 48. If the apertures 48 are in their closed position, ventilation will only occur within the lung communicating with the bronchus in which the expansive seal 30 is positioned.

Another embodiment of the airway assembly 10 is shown in FIGS. 15 through 21. This embodiment is substantially similar to the embodiment shown in FIGS. 8 through 14, hence the like reference numerals are used for similar structures. However, the embodiment illustrated in FIGS. 15 through 21 includes at least one aperture 48 and two seals, including a first expansive seal 30A and a second expansive seal 30B. Each of the seals 30, 30A and 30B are preferably similar construction and include at least one reinforcing member 38 as previously described. Both seals 30A and 30B are carried on the inner tube 12 and diametrically expand independently between expanded and collapsed positions, depending on relative position of the inner tube 12 and the outer tube 14. While FIGS. 15 and 21 show both seals 30A and 30B being simultaneously in the same position, either expanded or collapsed, it is to be noted that the expansive seal 30A may be in its expanded position while the expansive seal 30B is in its collapsed position, depending upon the relative position of the inner tube 12 relative to the outer tube 14. Significantly, as can be appreciated by considering FIGS. 15, 16 and 18, when expansive seal 30B is in its collapsed position, expansive seal 30B covers aperture 48 thereby restricting fluid flow through the aperture 48.

A further embodiment of the airway assembly 10 is shown in FIGS. 22 through 28. This embodiment is substantially similar to the embodiments shown in FIGS. 8 through 14. However, in this embodiment, both the expansive seal 30 and the inflatable member 40 are disposed on the inner tube 12 and in an order reversed from the order of those items as depicted in FIGS. 8 through 14. This embodiment demonstrates that elements of the airway assembly 10 may be arranged in any appropriately desired way to arrive at an airway assembly 10 that meets particular needs.

Drawing attention to FIG. 22, the inflation port 46 is associated with and positioned at a proximal end of the inner tube 12. A suitable conduit, not shown for clarity, is provided in association with the inner tube 12 for conveying fluid between the port 46 and the inflatable member 40 that is disposed on the inner tube 12 as described above. The expansive seal 30 is connected with the inner tube 12 at a position between the inflatable member 40 and the connector 24 relative to the longitudinal axis of the inner tube 12. The at least one aperture 48 passes through the inner tube 12 and is positioned such that the expansive seal 30, when in its collapsed position, covers and closes the at least one aperture 48. As discussed previously, the positions of the inflatable member 40 and the expansive seal 30 can be changed from what is shown in FIGS. 22 through 28. For example, the inflatable member 40 may be in its collapsed position while the expansive seal 30 is in its expanded position or the longitudinal spacing of the inflatable member 40 and expansive seal 30 along the longitudinal axis of the inner tube 12 may be altered.

An additional embodiment of the airway assembly 10 is shown in FIGS. 29 through 35. This embodiment is similar to the embodiment illustrated in FIGS. 8 through 14 in that both include an expansive seal 30, an inflatable member 40 and at least one aperture 48. However, in this embodiment, the expansive seal 30, the inflatable member 40 and the at least one aperture 48 are all disposed on the inner tube 12.

The inflation port 46 is disposed at a proximal end of the inner tube 12 proximate the connector 24. As described above with reference to other embodiments, a suitable inflation conduit, not shown for clarity, is associated with the inner tube 12 for conveying an inflation fluid between the inflation port 46 and the inflatable member 40 that is disposed on the inner tube 12 as well. The expansive seal 30 is disposed on the inner tube 12 such that the inflatable member 40 is located between the expansive seal 30 and the connector 24. The at least one aperture 48 passes through the inner tube 12 and is positioned between the expansive seal 30 and the inflatable member 40. In this configuration, fluid flow through the at least one aperture 48 is not dependent upon whether the expansive seal 30 is in its expanded or collapsed position. Fluid flow through the at least one aperture 48 is limited by appropriate relative positioning of the inner tube 12 and the outer tube 14, as shown in FIGS. 31 through 34.

With structure of the airway assembly 10 having been discussed with reference to the foregoing embodiments now an exemplary method of use of an airway assembly will be explained. To ease understanding, the embodiment of the airway assembly 10 similar to that shown in FIGS. 8 through 14 will be used. It is to be understood that any of the embodiments described herein can be used with this method with suitable modifications to either the method or to the assembly 10. Furthermore, additional features of the airway assembly 10 may become apparent to those skilled in the art upon review of the following description.

Beginning with FIG. 36, the airway assembly 10, including inner tube 12 and outer tube 14, is prepared for insertion into a patient to provide single or double lung ventilation. Positioning marks may be placed on the inner tube 12 to indicate to the physician the relative positions of the inner tube 12 and the outer tube 14 and whether the airway assembly 10 is in a single lung ventilation mode or in a dual lung ventilation mode. A first positioning mark 50 and a second positioning mark 52 indicate the status of the expansive seal 30 and the condition of the at least one aperture 48. Specifically, the first positioning mark 50 is provided distally to indicate that an expansive seal 30 is collapsed and within the outer tube 14, a first intermediate mark (not shown), proximal to the distal positioning mark 50, may indicate that the expansive seal 30 is expanded and that the at least one aperture 48 is closed and covered within the outer tube 14, a second intermediate mark (not shown), proximal to the first intermediate mark, may indicate that the expansive seal 30 is expanded and that the at least one aperture 48 is exposed and uncovered by the outer tube 14, and the second positioning mark 52 is provided proximally to indicate that the expansive seal 30 is expanded, the at least one aperture 48 is open and, where present, a proximal expansive seal is expanded. It will be understood that depending upon the specific configuration and number of expansive seals 30 and apertures 48, variations in the number and positioning of the positioning marks 50, 52 are contemplated in order to provide the physician with an indicator of the status of the respective expansive seals 30 or apertures 48.

When a proximal end 53 of the outer tube 14 is located distally of the first mark 50 (a first status of the airway assembly 10), the expansive seal 30 is in a collapsed position and the at least one aperture 48 is in its closed position. When a proximal end 53 of the outer tube 14 is adjacent the first mark 50 (a second status of the airway assembly 10), the expansive seal 30 is in its expanded position and the at lest one aperture 48 is in its close position. When in the second status of the airway assembly 10, ventilation of a single lung, through the inner tube 12 and the aperture 36 in the expansive seal 30, is possible. Ventilation of both lungs is accomplished by positioning the proximal end 53 of the outer tube 14 adjacent the second mark 52 (a third status of the airway assembly 10), the expansive seal 30 is in its expanded position and the at least one aperture 48 positioned in the inner tube 12 is in its open position, and the inflatable member 40 is inflated to seal the airway, thereby allowing an operator, such as a doctor and the like, of the airway assembly 10 to provide ventilation to both lungs. Thus, it can be appreciated that the first status of the airway assembly 10 corresponds to an initial status of the airway assembly 10, the second status of the airway assembly 10 corresponds to a single lung ventilation status of the airway assembly 10, and the third status of the airway assembly 10 corresponds to a dual lung ventilation status of the airway assembly 10. In some embodiments, there may be more or less marks provided on the inner tube 12 or the outer tube 14 or both, thereby providing more airway assembly 10 status indicators. In operation, the first mark 50 is a distal mark that indicates that the outer tube 14 is pulled back to expose the aperture 48, the inflation member 40 is expanded, and double lung ventilation is being performed. The second mark 53 is a proximal mark that indicates that the outer tube 14 is positioned to cover and close the aperture 48, the inflation member 40 is deflated, and the expansive seal 30 is deployed in a bronchi and single lung ventilation is being performed.

Figures 37, 37A:
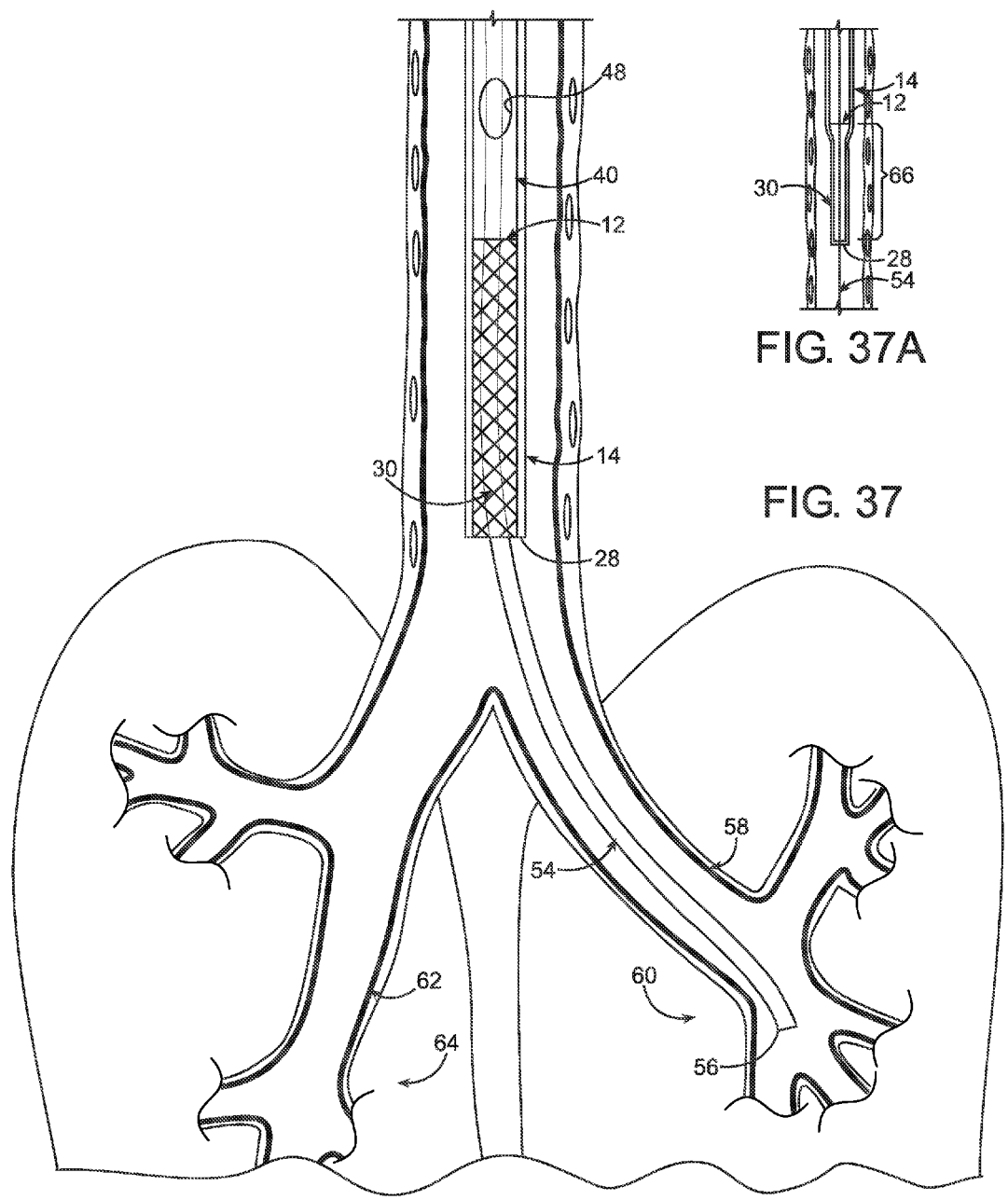
FIG. 37 is a diagrammatic view of a portion the airway assembly of FIG. 36 located within a patient.
FIG. 37A is a diagrammatic view of an embodiment of the airway assembly described herein.
Figure 38:
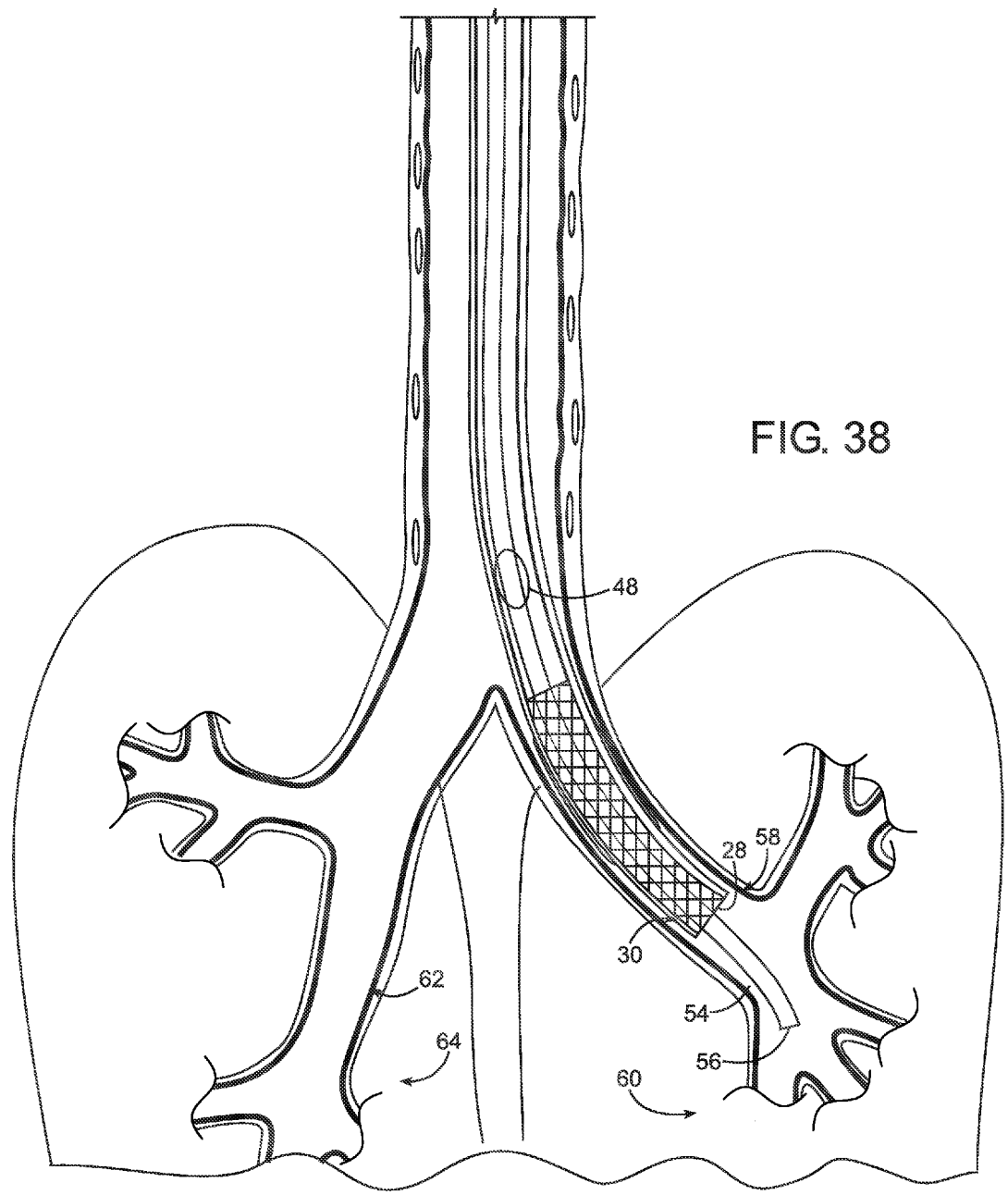
FIG. 38 is a diagrammatic view of a portion the airway assembly of FIG. 36 located within a patient.

As shown in FIGS. 36 through 38, after the airway assembly 10 is passed through the vocal chords using a laryngoscope, an endoscope 54, such as a bronchoscope and the like, is placed coaxially through the central lumen of the inner tube 12 to visualize distally the airway assembly 10 and provide placement guidance for the airway assembly 10. Once the intended position for placement of the expansive seal 30 is identified, the endoscope 54 acts like a guidewire for the airway assembly 10 to permit placement of the expansive seal 30 in the patient's right or left bronchial tree to permit single lung ventilation to the right or left lung respectively.

FIG. 37 illustrates portions of the airway assembly 10 and the endoscope 54 inserted into a patient. For ease of understanding, elements of the airway assembly 10 are represented transparently. A distal end 56 of the endoscope 54 is positioned within a first bronchus 58 of the patient. The first bronchus 58 is associated with a first lung 60. Of course, there is a second bronchus 62 associated with a second lung 64. The operator positions the distal end 56 of the endoscope 54 at a desired position in the first bronchus 58. The airway assembly 10 is advanced along the endoscope 54 to the desired position. As shown in FIG. 37A, some embodiments of the airway assembly 10 include a narrowed distal region 66, located adjacent distal ends, where the diameter of the inner tube 12 and the diameter of the outer tube 14 are reduced from other more proximal portions of those elements. In this embodiment, the expansive seal 30 may have an outer diameter within the range of about 10 to 15 mm. In some embodiments, the reduced dimensions are outer diameters which, adjacent distal ends, are smaller than outer diameters adjacent proximal ends of the same element, such as the inner tube 12, the outer tube 14 and the expansive seal 30. These reduced dimensions facilitate introduction of the airway assembly 10 into the patient by, for example, increasing ease of moving the distal end 28 of the outer tube 14 beyond vocal cords or glottic space of the patient. In some embodiments, the narrowed distal region 66 is substantially within the range of about 5 to about 8 cm in axial length, and has a maximum outer diameter substantially within the range of about 6 to about 10 mm. In some embodiments, when the expansive seal 30 is in its collapsed position, the expansive seal 30 has an outer diameter substantially equal to the outer diameter of the inner tube 12 adjacent the expansive seal 30.

To further facilitate introduction and maneuvering of the airway assembly 10, portions of the inner tube 12 and the outer tube 14 may be comprised of different materials having different physical and/or material properties. For example, proximal portions of the tubes 12 and 14 may be stiffer and more rigid than distal portions of the tubes 12 and 14. This construction may ease the advancement of the airway assembly 10 in the patient with reduced deformation or curving of the tubes 12 and 14. Further, the relatively softer and more malleable material comprising the distal portions of the tubes 12 and 14 may allow for deformation or compression of distal ends of the tubes 12 and 14, and also may be more accommodating to the operator.

In some embodiments, instead of having a tapered distal region 66, the inner tube 12 can have a substantially constant outer diameter similar to the outer diameter of the tapered distal region 66. This construction can reduce an outer diameter or profile of the airway assembly 10, and can facilitate aspiration through the space between the outer surface 18 of the inner tube 12 and the inner surface 20 of the outer tube 14. In other embodiments, both the inner tube 12 and the outer tube 14 can have substantially constant outer diameters, thereby making the region 66 unnecessary.

Figure 39:
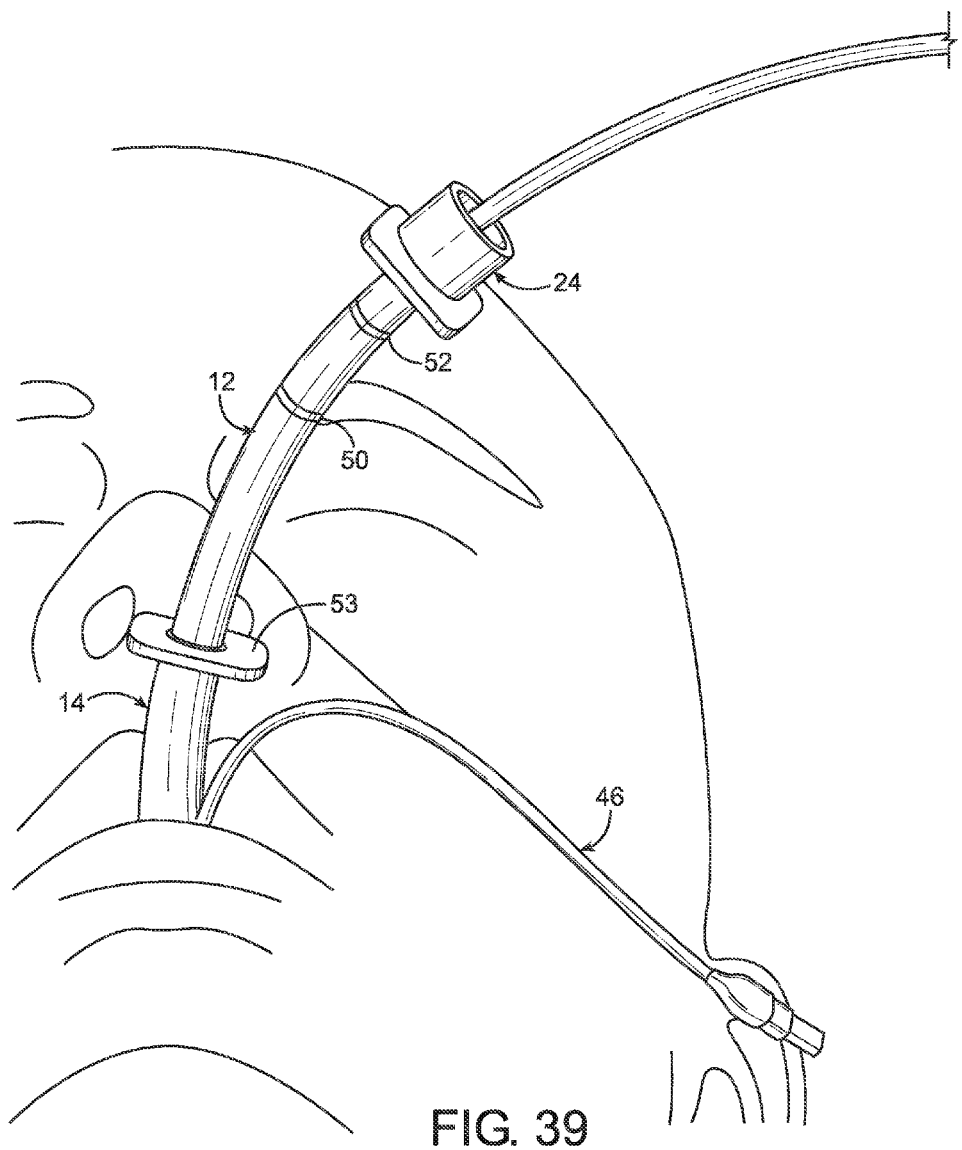
FIG. 39 is a diagrammatic view of a portion of an airway assembly described herein used with a patient.
Figure 40:
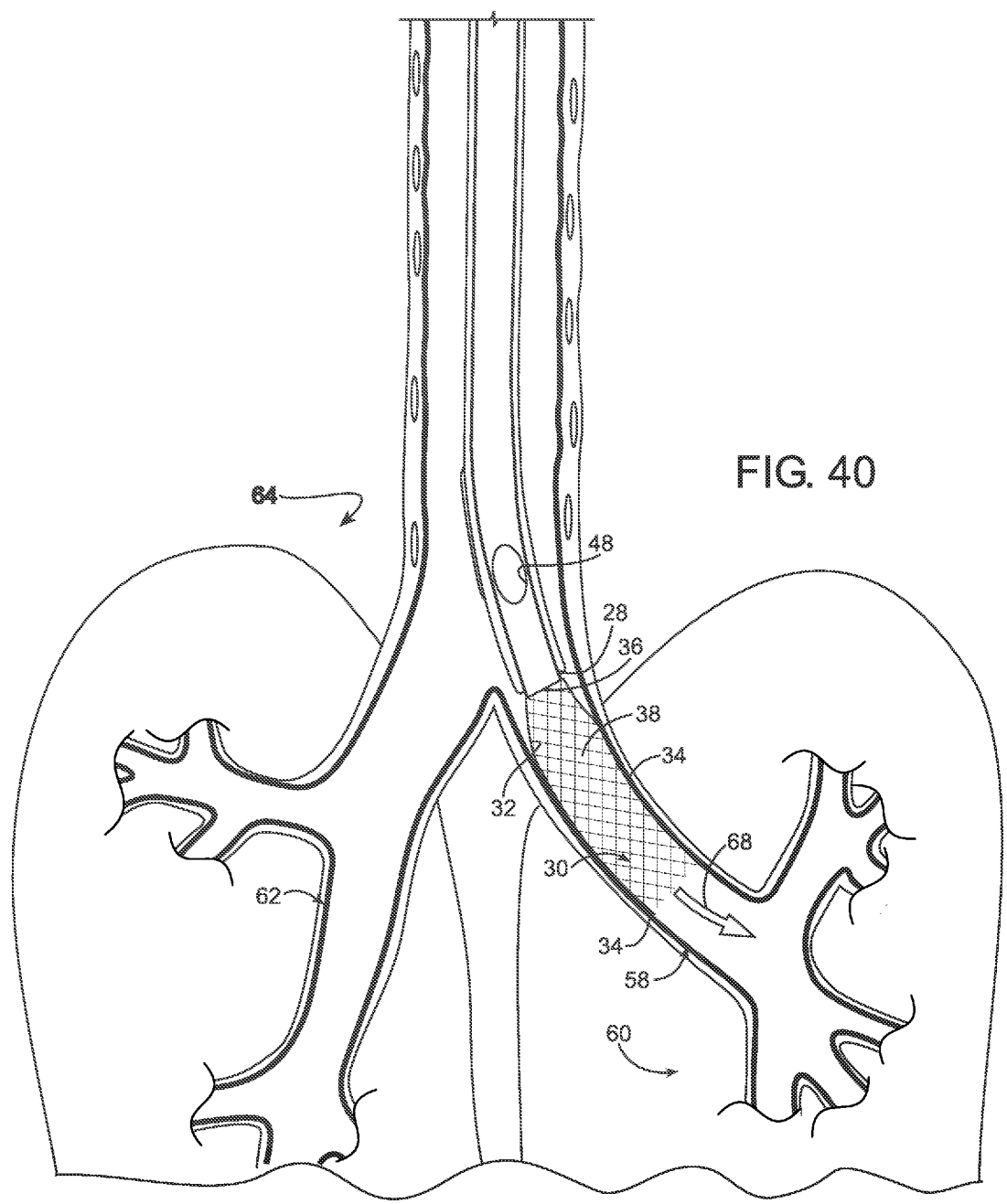
FIG. 40 is a diagrammatic view of a portion the airway assembly of FIG. 36 located within a patient.
Figure 41:
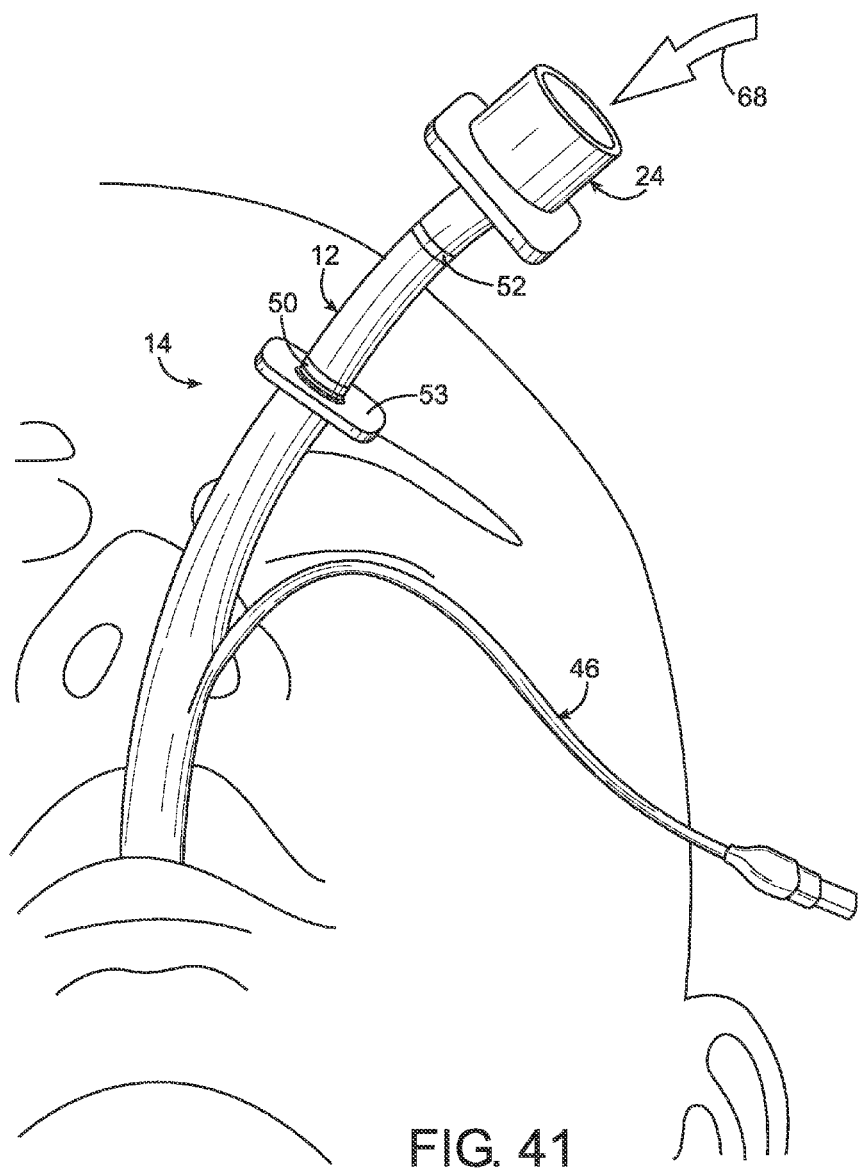
FIG. 41 is a diagrammatic view of a portion of an airway assembly described herein used with a patient.

As shown in FIG. 38, the airway assembly 10 is moved with respect to the patient to position the distal end 28 within the first bronchus 58. At this location, it is desired to move the expansive seal 30 from its collapsed position to its expanded position. Related conditions of a proximal end of the airway assembly 10 are shown in FIG. 39 (first location with expansive seal 30 collapsed) and FIG. 41 (second location with seal expanded). Note the relative locations of the marks 50 and 52 and the end 53. The outer tube 14 is moved to allow the expansive seal 30 to diametrically expand from its collapsed position to its expanded position. The endoscope 54 is then removed from the airway assembly 10 as shown in FIG. 40.

In its expanded position, the outer surface 34 of the expansive seal 30 contacts an inner surface of the first bronchus 58. The contact pressure between the outer surface 34 and the first bronchus 58 is sufficient to exclude secretions from passing across expansive seal 30 and into the first lung 60. However, that contact is insufficient to harm the first bronchus 58. With the expansive seal 30 in its expanded position, fluid can flow among the connector 24, the inner tube 12, the aperture 36, the first bronchus 58 and the first lung 60. This fluid flow is indicated generally by arrow 68 of FIGS. 40 and 41; under this condition the airway assembly is providing single lung ventilation to the first lung 60. This arrangement allows fluid to flow among the connector 24, the inner tube 12, the aperture 36, the first bronchus 58 and the first lung 60 while limiting fluid flow to or from the second bronchus 62 and the second lung 64. This configuration permits single lung ventilation while excluding ventilation to the other lung.

Figure 42:
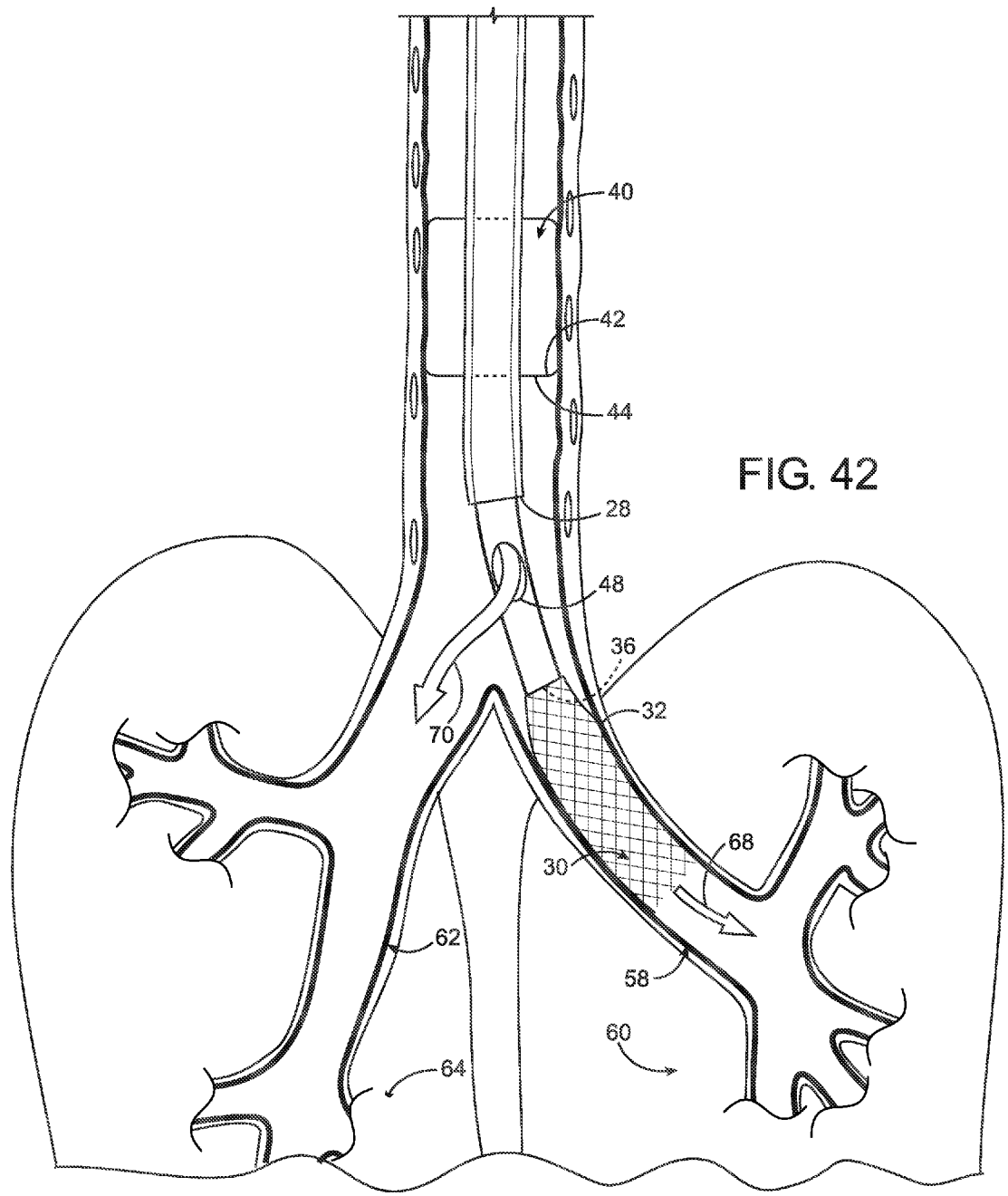
FIG. 42 is a diagrammatic view of a portion the airway assembly of FIG. 36 located within a patient.
Figure 43:
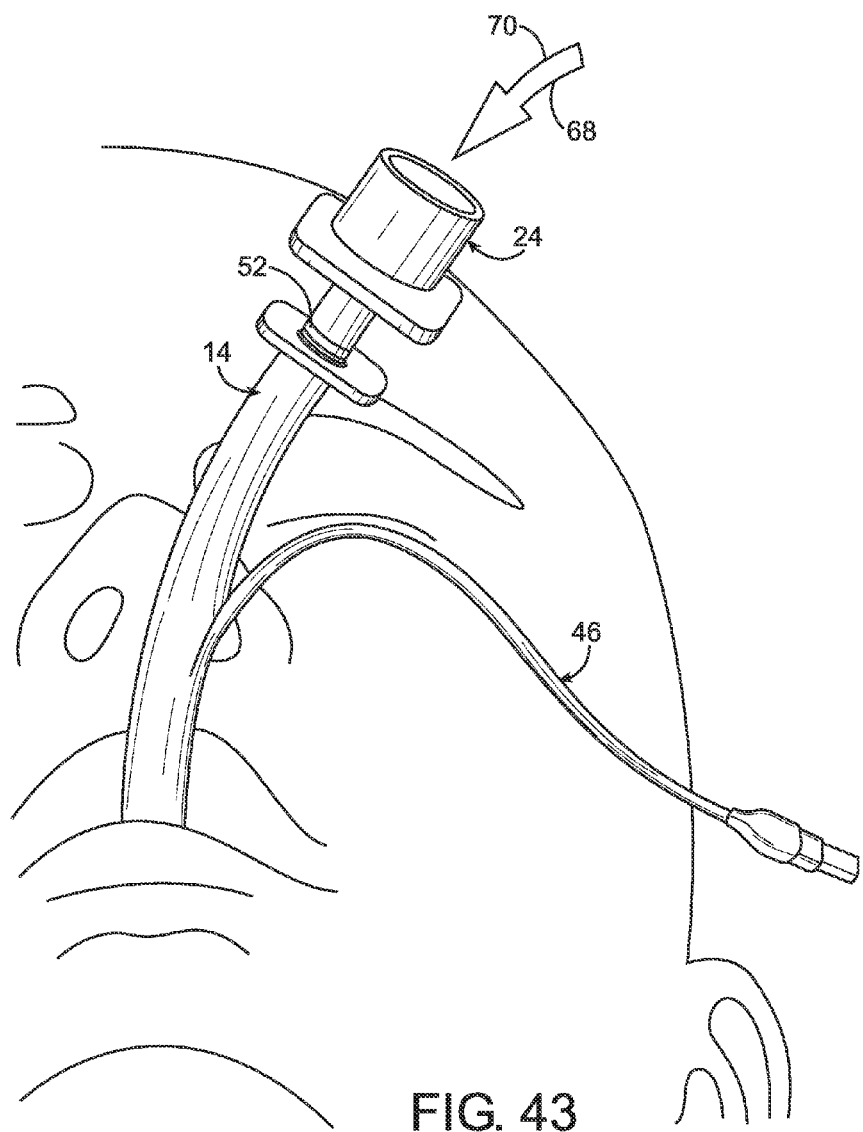
FIG. 43 is a diagrammatic view of a portion of an airway assembly described herein used with a patient.

It is not necessary to have the inflatable member 40 in its expanded position to ventilate a single lung. During single lung ventilation, the inflatable member 40 may be either in its deflated or inflated positions. When the patient's condition requires ventilation of both lungs, the outer tube 14 is moved with respect to the inner tube 12 so that the aperture 48 is moved to its open position. The proximal end 53 is adjacent the second mark 52. This is the third location (the at least one aperture 48 in its open position) and is shown in FIGS. 42 and 43. The inflatable member 40 is moved to its inflated position. By doing this, unintended back fluid flow is limited.

This status of the airway assembly 10 permits fluid flow among the connector 24, the inner tube 12, the aperture 48, the second bronchus 62 and the second lung 64. This fluid flow is represented by arrow 70 of FIG. 42. Fluid flow 68 occurs as well. The inflatable member 40 is changed to its inflated position. The proximal end of the airway assembly 10 is shown in FIG. 43. This configuration permits both lungs to be ventilated.

Figure 44:
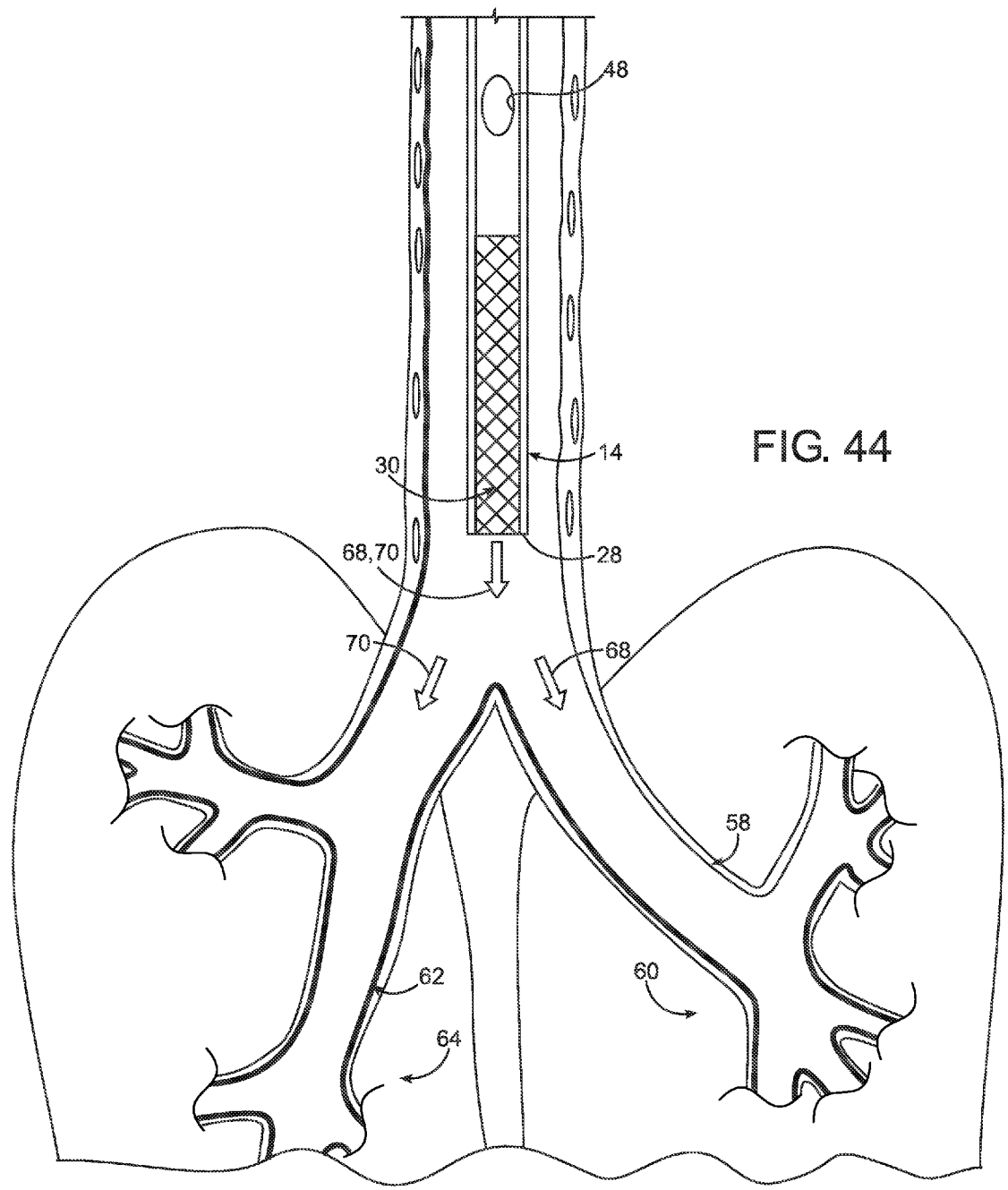
FIG. 44 is a diagrammatic view of a portion the airway assembly of FIG. 36 located within a patient.
Figure 45:
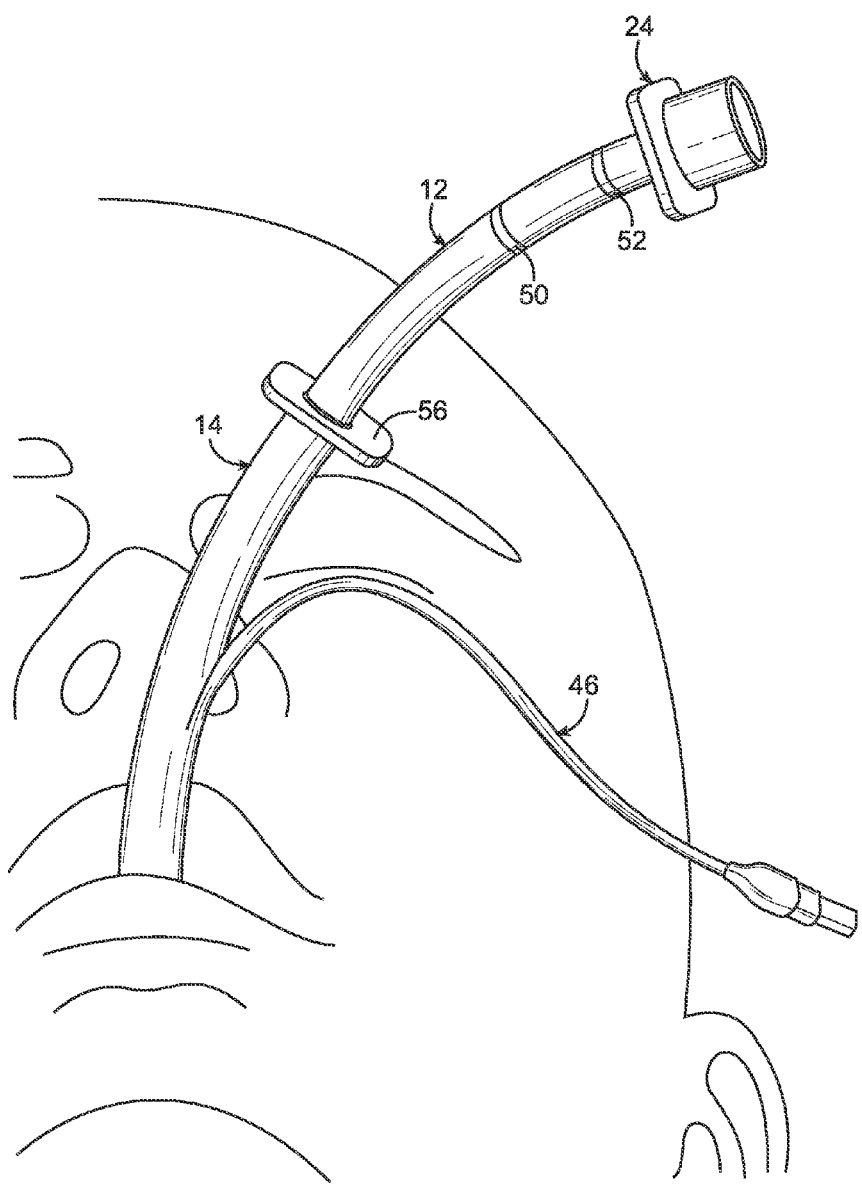
FIG. 45 is a diagrammatic view of a portion of an airway assembly described herein used with a patient.

When the clinical condition does not require single lung ventilation, such as at the end of a surgical procedure, as shown in FIG. 44, the inner tube 12 is moved pulled back proximally with respect to the outer tube 14 thereby capturing the expansive seal 30 within the outer tube 14 and collapsing the expansive seal 30. Fluid then flows to both the first lung 60 and the second lung 64. In this position, the airway assembly 10 is its delivery configuration, as shown in FIG. 45, and the airway assembly 10 may remain within the patient to provide continued intubation or the airway assembly 10 may be removed.

Those of ordinary skill in the art will understand and appreciate that the foregoing description of the invention has been made with reference to certain exemplary embodiments of the invention, which describe airway assemblies suitable for single and/or dual lung ventilation, while excluding passage of secretions across the expansive seal 30. Those of skill in the art will understand that obvious variations in construction, materials, dimensions or properties may be made without departing from the scope of the invention which is intended to be limited only by the claims appended hereto.

What is claimed is:

1. An airway assembly insertable into an airway, the airway assembly comprising:
    (a) an outer tube having walls and a central lumen;
    (b) an inner tube having walls and a central lumen and being coaxially disposed within the central lumen of the outer tube; and
    (c) a diametrically expansive seal positioned at a distal end of the inner tube and the diametrically expansive seal including at least one reinforcing member extending along the longitudinal length of the diametrically expansive seal, the diametrically expansive seal being movable between a collapsed position and an expanded position, whereby the at least one reinforcing member facilitates diametrically expansive movement of the diametrically expansive seal between the collapsed position and the expanded position, and where the diametrically expansive seal is adapted to sealingly seat against an anatomical airway passage;
wherein the inner tube and the outer tube have proximal portions and distal portions, and wherein outer diameters of the distal portions are smaller than outer diameters of the proximal portions.

2. The airway assembly as defined in claim 1, wherein the inner tube and the outer tube are coaxially movable relative to each other and the diametrically expansive seal diametrically expands and collapses in response to the relative coaxial movement of the inner tube and the outer tube.

3. The airway assembly as defined in claim 1, wherein the diametrically expansive seal further comprises a plurality of reinforcing members in a radially spaced apart relationship relative to adjacent reinforcing members and operably associated with the diametrically expansive seal that facilitates diametrically expansive movement of the diametrically expansive seal between the collapsed position and the expanded position and exerts a sealing pressure of the diametrically expansive seal for sealing against the airway sufficient to retard fluid from passing across the diametrically expansive seal.

4. The airway assembly as defined in claim 3, wherein the diametrically expansive seal further comprises a generally tubular member having walls, a proximal end fixedly coupled to the inner tube and an uncoupled distal end, wherein the walls and the distal end of the generally tubular member diametrically expand such that the distal end forms a diametrically enlarged distal opening adapted to sealingly seat against the airway and in fluid flow communication with the airway.

5. The airway assembly as defined in claim 4, wherein the proximal end of the diametrically expansive seal is coupled to a distal end of the inner tube and is in fluid flow communication with the central lumen of the inner tube.

6. The airway assembly as defined in claim 1, further comprising:
(d) an aperture disposed on the diametrically expansive seal, and wherein the aperture is fluidly connected with the inner tube to permit fluid flow between the inner tube and the aperture.

7. The airway assembly as defined in claim 1, further comprising:
d) a first position mark disposed on a wall surface of the inner tube; and
e) a second position mark disposed on a wall surface of the inner tube, wherein a proximal end of the outer tube is adjacent the first position mark when the diametrically expansive seal is in its collapsed position, and wherein the proximal end of the outer tube is adjacent the second position mark when the diametrically expansive seal is in the expanded position.

8. The airway assembly as defined in claim 7, further comprising:
(f) an aperture passing through a distal portion of the inner tube, and wherein the aperture is in an open position when the proximal end of the outer tube is adjacent the second position mark.

9. The airway assembly as defined in claim 1, further comprising:
(d) a second diametrically expansive seal operably associated with the inner tube, the second diametrically expansive seal being movable between a collapsed position and an expanded position where the second diametrically expansive seal engages the airway.

10. The airway assembly as defined in claim 9, further comprising:
(d) an aperture passing through a wall of the inner tube, wherein fluid flow through the aperture is permitted when the second diametrically expansive seal is in the expanded position and wherein fluid flow through the aperture is restricted when the second diametrically expansive seal is in the collapsed position.

11. The airway assembly as defined in claim 1, wherein the distal portions of the inner tube and outer tube have greater flexibility relative to the proximal portions of the inner tube and outer tube.

12. The airway assembly as defined in claim 1, wherein the outer tube further comprises a fluid flow port operably associated with the proximal portion of the outer tube and in fluid flow communication with the central lumen of the outer tube and external the outer tube.

13. The airway assembly as defined in claim 12, wherein the outer tube further comprises at least one aperture passing through a distal portion of the wall of the outer tube and in fluid flow communication between the central lumen of the outer tube and the fluid flow port.

14. The airway assembly as defined in claim 1, wherein the diametrically expansive seal further comprises at least one of a radiographic marker and a fluoroscopic marker.

15. The airway assembly as defined in claim 1, further comprising:
(d) a plurality of perforations passing through a distal portion of the outer tube and communicating with a space between the inner tube and the outer tube.

16. An airway assembly insertable into an airway, the airway assembly comprising:
a) an outer tube having a proximal portion and a distal portion;
b) an inner tube disposed coaxially with the outer tube, the inner tube having a proximal portion and a distal portion; wherein the distal portion of the outer tube has an outer diameter smaller than an outer diameter of the proximal portion of the outer tube, and the distal portion of the inner tube has an outer diameter smaller than an outer diameter of the proximal portion of the inner tube; and
c) a generally tubular diametrically expansive seal coupled at its proximal end to the inner tube, the generally tubular diametrically expansive seal including at least one reinforcing member extending along the longitudinal length of the generally tubular diametrically expansive seal, at least one reinforcing member to facilitate diametrically expansive movement of the generally tubular diametrically expansive seal to an expanded outer diameter sufficient for sealingly engaging the airway and an open distal end in fluid flow communication with the airway.

17. The airway assembly as defined in claim 16, wherein the inner tube further comprises at least one aperture passing through a wall surface of the inner tube distally along a longitudinal length of the inner tube, the at least one aperture having an open position and a closed position depending on relative axial positions of the inner tube and the outer tube.

18. The airway assembly as defined in claim 17, further comprising an inflatable member operably disposed on a distal portion of the outer tube, the inflatable member being movable between a deflated position and an inflated position where the inflatable member sealingly engages the airway.

19. The airway assembly as defined in claim 18, wherein the inflatable member is positioned proximal the generally tubular diametrically expansive seal on the inner tube.

20. The airway assembly as defined in claim 19, wherein the at least one aperture is positioned proximal the generally tubular diametrically expansive seal.

21. The airway assembly as defined in claim 17, further comprising an inflatable member operably disposed on a distal portion of the inner tube, the inflatable member being moveable between a deflated position and an inflated position where the inflatable member sealingly engages the airway.

22. The airway assembly as defined in claim 21, wherein the at least one aperture is positioned proximal the inflatable member and distal a coupling between the proximal end of the generally tubular diametrically expansive seal and the inner tube.

23. The airway assembly as defined in claim 22, wherein the at least one aperture is positioned underneath the generally tubular diametrically expansive seal such that in the closed position of the at least one aperture the generally tubular diametrically expansive seal is in a collapsed position covering the at least one aperture and in the open position of the at least one aperture the generally tubular diametrically expansive seal is in an expanded position.

24. The airway assembly as defined in claim 16, wherein the inner tube is co-axially movable within a central lumen of the outer tube, and wherein the diametrically expansive seal moves between the collapsed position and the expanded position responsive to relative movement of the inner tube and the outer tube.

25. The airway assembly as defined in claim 24, wherein the generally tubular diametrically expansive seal comprises a first diametrically expansive seal coupled to a distal end of the inner tube and communicating with a central lumen of the inner tube and further comprises a second diametrically expansive seal positioned proximate the first diametrically expansive seal and coupled to the inner tube and at least one aperture passing through the inner tube and communicating with the central lumen of the inner tube, the at least one aperture being positioned underneath the second diametrically expansive seal such when the second diametrically expansive seal is in a collapsed position the at least one aperture is in a closed position and when the second diametrically expansive seal is in a diametrically expanded position, the at least one aperture is in a open position to communicate fluid flow to and from the airway through a space defined within the second diametrically expansive seal, through the at least one aperture and into the central lumen of the inner tube.

26. The airway assembly defined in claim 25, wherein the first diametrically expansive seal and the second diametrically expansive seal each further comprise at least one reinforcing member that facilitates diametrically expansive movement of the first diametrically expansive seal and the second diametrically expansive seal between the collapsed position and the expanded position and that exerts a sealing pressure of the first diametrically expansive seal and the second diametrically expansive seal against the airway sufficient to retard fluid from passing across the first diametrically expansive seal and the second diametrically expansive seal.

27. The airway assembly defined in claim 16, wherein the generally tubular diametrically expansive seal further comprises a plurality of reinforcing members in a radially spaced apart relationship relative to adjacent reinforcing members and operably associated with the generally tubular diametrically expansive seal that facilitates diametrically expansive movement of the generally tubular diametrically expansive seal between a collapsed position and an expanded position that exerts a sealing pressure of the generally tubular diametrically expansive seal for sealing against the airway sufficient to retard fluid from passing across the generally tubular diametrically expansive seal.

28. The airway assembly as defined in claim 16, wherein the inner tube further comprises:
  (i) a first position mark disposed a proximal end of the inner tube indicating a diametrically expanded position of the expansive seal when the outer tube is relatively positioned at the first position mark; and
  (ii) a second position mark disposed at a proximal end of the inner tube and in spaced apart relationship from the first position mark indicating a diametrically expanded position of the expansive seal and an open position of at least one aperture in the inner tube proximal to the seal when the outer tube is relatively positioned at the second position mark.

29. The airway assembly as defined in claim 16, wherein the diametrically expansive seal further comprises at least one of a radiographic marker and a fluoroscopic marker.

30. The airway assembly as defined in claim 16 wherein proximal portions of each of the inner tube and the outer tube are more rigid than distal portions of the inner tube and the outer tube.

* * * * *